US012246063B2

(12) United States Patent
Friedman et al.

(10) Patent No.: US 12,246,063 B2
(45) Date of Patent: Mar. 11, 2025

(54) IMMUNOGEN PROVIDING AN EXTENDED PROTECTIVE LIFETIME AGAINST RESPIRATORY SYNCYTIAL VIRUS (RSV) AND VACCINES THEREOF

(71) Applicant: Trellis Bioscience, LLC, Redwood City, CA (US)

(72) Inventors: Milton J. Friedman, Alameda, CA (US); Lawrence M. Kauvar, San Francisco, CA (US)

(73) Assignee: Trellis Bioscience, Inc., Redwood City, CA (US)

( * ) Notice: Subject to any disclaimer, the term of this patent is extended or adjusted under 35 U.S.C. 154(b) by 1011 days.

(21) Appl. No.: 17/168,553

(22) Filed: Feb. 5, 2021

(65) Prior Publication Data

US 2021/0268096 A1    Sep. 2, 2021

Related U.S. Application Data

(63) Continuation of application No. PCT/US2019/045775, filed on Aug. 8, 2019.

(60) Provisional application No. 62/716,184, filed on Aug. 8, 2018.

(51) Int. Cl.
*A61K 39/12* (2006.01)
*A61K 39/00* (2006.01)
*A61P 31/14* (2006.01)

(52) U.S. Cl.
CPC .............. *A61K 39/12* (2013.01); *A61P 31/14* (2018.01); *A61K 2039/545* (2013.01); *A61K 2039/6056* (2013.01)

(58) Field of Classification Search
CPC .............. A61K 39/12; A61K 2039/545; A61K 2039/6056; A61P 31/14
See application file for complete search history.

(56) References Cited

U.S. PATENT DOCUMENTS

| 6,077,511 | A | 6/2000 | Langedijk | |
|---|---|---|---|---|
| 7,323,172 | B2 | 1/2008 | Young | |
| 7,736,648 | B2 * | 6/2010 | Kauvar | C07K 16/1027 435/69.6 |
| 8,173,131 | B2 | 5/2012 | Tripp | |
| 8,273,354 | B2 | 9/2012 | Kauvar | |
| 8,846,056 | B2 | 9/2014 | Anderson | |
| 9,321,830 | B2 | 4/2016 | Kauvar | |
| 9,718,875 | B2 | 8/2017 | Wittekind | |
| 10,035,842 | B2 | 7/2018 | Wadia | |
| 2004/0009177 | A1 | 1/2004 | Tripp | |
| 2004/0096451 | A1 | 5/2004 | Young | |
| 2005/0042230 | A1 | 2/2005 | Anderson | |
| 2006/0018925 | A1 | 1/2006 | Tripp | |
| 2013/0034564 | A1 | 2/2013 | Kauvar | |
| 2013/0136759 | A1 | 5/2013 | Anderson | |
| 2017/0121394 | A1 | 5/2017 | Vora | |
| 2019/0055545 | A1 | 2/2019 | Elledge | |
| 2019/0135876 | A1 | 5/2019 | Dubois | |

FOREIGN PATENT DOCUMENTS

| JP | 2000512136 | 9/2000 |
|---|---|---|
| JP | 2007505033 | 3/2007 |
| JP | 2011500091 | 1/2011 |
| JP | 2021531465 | 11/2021 |
| WO | 1997046581 | 12/1997 |
| WO | 2005007189 | 1/2005 |
| WO | 2009055711 | 4/2009 |
| WO | 2012006395 | 1/2012 |
| WO | 2017075124 | 5/2017 |

OTHER PUBLICATIONS

Collarini et al. Potent High-Affinity Antibodies for Treatment and Prophylaxis of Respiratory Syncytial Virus Derived From B Cells of Infected Patients. J Immunol. Nov. 15, 2009; 183(10): 6338-45. (Year: 2009).
Communication pursuant to Rule 164(1) EPC, Partial Supplementary Search Report, issued in EP18865711.8 on Jun. 21, 2021.
Fedechkin, S. et al., "Conformational Flexibility in Respiratory Syncytial Virus G Neutralizing Epitopes." J Virol. Feb. 28, 2020; 94(6):e01879-19.
Jorquera, P., et al., "Respiratory syncytial virus: prospects for new and emerging therapeutics." Expert Rev Respir Med. Aug. 2017; 11(8):609-615.
Jorquera, P., et al., "Understanding respiratory syncytial virus (RSV) vaccine development and aspects of disease pathogenesis." Expert Rev Vaccines. 2016; 15(2):173-87.
Manning et al. Stability of Protein Pharmaceutical: An Update. Pharmaceutical Research, vol. 27, No. 4, Apr. 2010 (Year: 2010).
Murata et al., "Humoral response to the central unglycosylated region of the respiratory syncytial virus attachment protein", Vaccine. Aug. 31, 2010;28(38):6242-6. doi: 10.1016/j.vaccine.2010.07.011. Epub Jul. 23, 2010.
Scheiblhofer et al. Influence of protein fold stability on immunogenicity and its implications for vaccine design. Expert Rev Vaccines. May 2017; 16(5) :479-489. doi: 10.1080/14760584.2017.1306441. Epub Mar. 24, 2017. (Year: 2017).
Tripp, R., et al., "Respiratory Syncytial Virus: Targeting the G Protein Provides a New Approach for an Old Problem." Journal of virology vol. 92, 3 e01302-17. Jan. 17, 2018.
Youngjoo et al., "Antibodies to the central conserved region of respiratory syncytial virus (RSV) G protein block RSV G protein CX3C-CX3CR1 binding and cross-neutralize RSV A and B strains", Viral Immunol. Jun. 2012;25 (3):193-203. doi: 10.1089/vim.2011.0094. Epub May 2, 2012.

(Continued)

Primary Examiner — Robert S Landsman
(74) Attorney, Agent, or Firm — FisherBroyles, LLP; Adam K. Whiting; Adelaide K. Leitzel

(57) ABSTRACT

Improvements to vaccines against RSV include G protein CCD portions complexed with mAb that block interaction with CX3C-R and modified forms of mAb to prolong serum half-life, as well as inhalable vaccines.

17 Claims, No Drawings
Specification includes a Sequence Listing.

(56) References Cited

OTHER PUBLICATIONS

Zhang et al., Vaccination to induce antibodies blocking the CX3C-CX3CR1 interaction of respiratory syncytial virus G protein reduces pulmonary inflammation and virus replication in mice, Journal of Virology, 2010, 84(2) 1148-1157.
Jorquera et al., Layer-by-layer nanoparticle vaccines carrying the G protein CX3C motif protect against RSV infection and disease, Vaccines, 2015, 3, 829-849.
Robbie, Gabriel J., et al., Antimicrobial Agents and Chemotherapy, Dec. 2013, vol. 57, No. 12, pp. 6147-6153, DOI: 10.1128/AAC.01285-13.
Fedechkin, Stanislav O., et al., Science Immunology, Mar. 9, 2018, vol. 3, No. 21, Article No. eaar3534, DOI: 10.1126/sciimmunol.aar3534.
Kruijsen, Debby, et al., Journal of Virology, Jul. 2013, vol. 87, No. 13, pp. 7550-7557, DOI: 10.1128/JVI.00493-13.
Abdel-Motal, et al., "Mechanism for increased immunogenicity of vaccines that form in vivo immune complexes with the natural anti-Gal antibody", Vaccine. May 18, 2009;27(23):3072-82. doi: 10.1016/j.vaccine.2009.03.019. Epub Mar. 28, 2009.
Abhinandan et al., "Analysis and improvements to Kabat and structurally correct numbering of antibody variable domains", Mol Immunol. Aug. 2008;45(14):3832-9. doi: 10.1016/j.molimm.2008.05.022. Epub Jul. 9, 2008.
American Academy of Pediatrics Committee on Infectious Diseases, "Updated guidance for palivizumab prophylaxis among infants and young children at increased risk of hospitalization for respiratory syncytial virus infection", Pediatrics. Aug. 2014;134(2):e620-38. doi: 10.1542/peds.2014-1666.
Ari and Fink, "Aerosol Delivery Devices for the Treatment of Adult Patients in Acute and Critical Care", Curr Pharm Biotechnol. 2016;17(14):1268-1277.
Arnold et al., "Respiratory syncytial virus deficient in soluble G protein induced an increased proinflammatory response in human lung epithelial cells", Virology. Dec. 20, 2004;330(2):384-97. doi: 10.1016/j.virol.2004.10.004.
Azhar et al, "Recent advances in the development of novel protein scaffolds based therapeutics", Int J Biol Macromol. Sep. 2017;102:630-641. doi: 10.1016/j.ijbiomac.2017.04.045. Epub Apr. 13, 2017.
Balazs, et al., "Vectored immunoprophylaxis protects humanized mice from mucosal HIV transmission", Nat Med. Mar. 2014;20(3):296-300. doi: 10.1038/nm.3471. Epub Feb. 9, 2014.
Balazs, et al., "Antibody-based protection against HIV infection by vectored immunoprophylaxis", Nature. Nov. 30, 2011;481(7379):81-4. doi: 10.1038/nature10660.
Bates, et al., "Escape from neutralization by the respiratory syncytial virus-specific neutralizing monoclonal antibody palivizumab is driven by changes in on-rate of binding to the fusion protein", Virology. Apr. 2014;454-455:139-44. doi: 10.1016/j.virol.2014.02.010. Epub Mar. 3, 2014.
Biggar, et al., "Real-time protein unfolding: a method for determining the kinetics of native protein denaturation using a quantitative real-time thermocycler", Biotechniques. Oct. 2012;53(4):231-8. doi: 10.2144/0000113922.
Boyoglu-Barnum, et al., "Mutating the CX3C Motif in the G Protein Should Make a Live Respiratory Syncytial Virus Vaccine Safer and More Effective", J Virol. Apr. 28, 2018;91(10):e02059-16. doi: 10.1128/JVI.02059-16. Print May 15, 2017.
Brady, L.J., "Antibody-mediated immunomodulation: a strategy to improve host responses against microbial antigens", Infect Immun. Feb. 2005;73(2):671-8. doi: 10.1128/IAI.73.2.671-678.2005.
Brint, et al., "Prolonged viral replication and longitudinal viral dynamic differences among respiratory syncytial virus infected infants", Pediatr Res. Nov. 2017;82(5):872-880. doi: 10.1038/pr.2017.173. Epub Aug. 9, 2017.
Broadbent, et al., "Respiratory syncytial virus, an ongoing medical dilemma: an expert commentary on respiratory syncytial virus prophylactic and therapeutic pharmaceuticals currently in clinical trials", Influenza Other Respir Viruses. Jul. 2015;9(4):169-78. doi: 10.1111/irv.12313.
Buonaguro, et al., "Developments in virus-like particle-based vaccines for infectious diseases and cancer", Expert Rev Vaccines. Nov. 2011;10(11):1569-83. doi: 10.1586/erv.11.135.
Choi, et al., "Antibodies to the central conserved region of respiratory syncytial virus (RSV) G protein block RSV G protein CX3C-CX3CR1 binding and cross-neutralize Rsv A and B strains", Viral Immunol. Jun. 2012;25(3):193-203. doi: 10.1089/vim.2011.0094. Epub May 2, 2012.
Chothia, et al., "Canonical structures for the hypervariable regions of immunoglobulins", J Mol Biol. Aug. 20, 1987;196(4):901-17. doi: 10.1016/0022-2836(87)90412-8.
Chothia, et al., "Conformations of immunoglobulin hypervariable regions", Nature. Dec. 21-28, 1989;342(6252):877-83. doi: 10.1038/342877a0.
Collarini, et al., "Potent high-affinity antibodies for treatment and prophylaxis of respiratory syncytial virus derived from B cells of infected patients", J Immunol. Nov. 15, 2009;183(10):6338-45. doi: 10.4049/jimmunol.0901373. Epub Oct. 19, 2009.
Colosia, et al., "The epidemiology of medically attended respiratory syncytial virus in older adults in the United States: A systematic review", PLoS One. Aug. 10, 2017;12(8):e0182321. doi: 10.1371/journal.pone.0182321. eCollection 2017.
Dorgham, et al., "An engineered CX3CR1 antagonist endowed with anti-inflammatory activity", J Leukoc Biol. Oct. 2009;86(4):903-11. doi: 10.1189/jlb.0308158. Epub Jul. 1, 2009.
Falsey, et al., "Respiratory syncytial virus infection in elderly and high-risk adults", N Engl J Med. Apr. 28, 2005;352(17):1749-59. doi: 10.1056/NEJMoa043951.
Fedechkin et al., "Structures of respiratory syncytial virus G antigen bound to broadly neutralizing antibodies", Sci Immunol., Mar. 9, 2018;3(21):eaar3534. doi: 10.1126/sciimmunol.aar3534. Epub Mar. 9, 2018.
Gaillard, et al., "A Short Double-Stapled Peptide Inhibits Respiratory Syncytial Virus Entry and Spreading", Antimicrob Agents Chemother. Mar. 24, 2017;61(4):e02241-16. doi: 10.1128/AAC.02241-16. Print Apr. 2017.
Gelfand, E.W., "Development of asthma is determined by the age-dependent host response to respiratory virus infection: therapeutic implications", Curr Opin Immunol. Dec. 2012;24(6):713-9. doi: 10.1016/j.coi.2012.08.011. Epub Sep. 13, 2012.
Gottlieb, et al., "ALN-RSV01 for prevention of bronchiolitis obliterans syndrome after respiratory syncytial virus infection in lung transplant recipients", J Heart Lung Transplant. Feb. 2016;35(2):213-21. doi: 10.1016/j.healun.2015.08.012. Epub Sep. 3, 2015.
Griffin, et al., "Safety, Tolerability, and Pharmacokinetics of MEDI8897, the Respiratory Syncytial Virus Prefusion F-Targeting Monoclonal Antibody with an Extended Half-Life, in Healthy Adults", Antimicrob Agents Chemother. Feb. 23, 2017;61(3):e01714-16. doi: 10.1128/AAC.01714-16. Print Mar. 2017.
Hall, et al., "The burden of respiratory syncytial virus infection in young children", N Engl J Med. Feb. 5, 2009;360(6):588-98. doi: 10.1056/NEJMoa0804877.
Hendricks, et al., "Further characterization of the soluble form of the G glycoprotein of respiratory syncytial virus", J Virol. Jul. 1988;62(7):2228-33. doi: 10.1128/JVI.62.7.2228-2233.1988.
Houston et al., "Inactivated Venezuelan equine encephalomyelitis virus vaccine complexed with specific antibody: enhanced primary immune response and altered pattern of antibody class elicited", J Infect Dis. Apr. 1977; 135(4):600-10. doi: 10.1093/infdis/135.4.600.
International Search Report and Written Opinion issued in PCT/US2019/045775 on Nov. 8, 2019 (11 pages).
Jeong, et al., "CX3CR1 Is Expressed in Differentiated Human Ciliated Airway Cells and Co-Localizes with Respiratory Syncytial Virus on Cilia in a G Protein-Dependent Manner", PLoS One. Jun. 24, 2015;10(6):e0130517. doi: 10.1371/journal.pone.0130517. eCollection 2015.
Johnson, et al., "Respiratory Syncytial Virus Uses CX3CR1 as a Receptor on Primary Human Airway Epithelial Cultures", PLoS Pathog. Dec. 11, 2015;11(12):e1005318. doi: 10.1371/journal.ppat.1005318. eCollection Dec. 2015.

(56) References Cited

OTHER PUBLICATIONS

Jones, et al., "Structural basis for recognition of the central conserved region of RSV G by neutralizing human antibodies", PLoS Pathog. Mar. 6, 2018;14(3):e1006935. doi: 10.1371/journal.ppat. 1006935. eCollection Mar. 2018.

Jorquera, et al., "Nanoparticle vaccines encompassing the respiratory syncytial virus (RSV) G protein CX3C chemokine motif induce robust immunity protecting from challenge and disease", PLoS One. Sep. 10, 2013;8(9):e74905. doi: 10.1371/journal.pone.0074905. eCollection 2013.

Jorquera and Tripp, "Respiratory syncytial virus: prospects for new and emerging therapeutics", Expert Rev Respir Med. Aug. 2017;11(8):609-615. doi: 10.1080/17476348.2017.1338567. Epub Jun. 14, 2017.

Kelly and Price, "The application of circular dichroism to studies of protein folding and unfolding", Biochim Biophys Acta. Apr. 4, 1997;1338(2):161-85. doi: 10.1016/s0167-4838(96)00190-2.

Kim, et al. , "Respiratory syncytial virus disease in infants despite prior administration of antigenic inactivated vaccine", Am J Epidemiol, . Apr. 1969;89(4):422-34. doi: 10.1093/oxfordjournals.aje.a120955. Abstract Only.

Kontermann, R.E., "Strategies to extend plasma half-lives of recombinant antibodies", BioDrugs. 2009;23(2):93-109. doi: 10.2165/ 00063030-200923020-00003.

Kruij sen, et al., :Intranasal administration of antibody-bound respiratory syncytial virus particles efficiently primes virus-specific immune responses in mice, J Virol. Jul. 2013;87(13):7550-7. doi: 10.1128/JVI.00493-13. Epub May 1, 2013.

Lambour, et al. "Converting monoclonal antibody-based immunotherapies from passive to active: bringing immune complexes into play", Emerg Microbes Infect. Aug. 17, 2016;5(8):e92. doi: 10.1038/emi.2016.97.

Lee and Chang, "Universal vaccine against respiratory syncytial virus A and B subtypes", PLoS One. Apr. 6, 2017;12(4):e0175384. doi: 10.1371/journal.pone.0175384. eCollection 2017.

Lieberman-Blum, et al. , "Maraviroc: a CCR5-receptor antagonist for the treatment of HIV-1 infection", Clin Ther. Jul. 2008;30(7):1228-50. doi: 10.1016/s0149-2918(08)80048-3.

Malm, et al., "Engineering of a bispecific affibody molecule towards HER2 and HER3 by addition of an albumin-binding domain allows for affinity purification and in vivo half-life extension", Biotechnol J. Sep. 2014;9(9):1215-22. doi: 10.1002/biot.201400009. Epub Apr. 23, 2014.

McClellan, et al., "Structure of RSV fusion glycoprotein trimer bound to a prefusion-specific neutralizing antibody", Science. May 31, 2013;340(6136):1113-7. doi: 10.1126/science.1234914. Epub Apr. 25, 2013.

Meissner and Kimberlin, "RSV immunoprophylaxis: does the benefit justify the cost?", Pediatrics. Nov. 2013; 132(5):915-8. doi: 10.1542/peds.2013-2449. Epub Oct. 14, 2013.

Nair, et al., "Global burden of acute lower respiratory infections due to respiratory syncytial virus in young children: a systematic review and meta-analysis", Lancet. May 1, 2010;375(9725):1545-55. doi: 10.1016/S0140-6736(10)60206-1.

Oshansky, et al., "Respiratory syncytial virus proteins modulate suppressors of cytokine signaling 1 and 3 and the type I interferon response to infection by a toll-like receptor pathway", Viral Immunol. Jun. 2009;22(3):147-61. doi: 10.1089/vim.2008.0098.

Ramilo, et al., "Motavizumab treatment of infants hospitalized with respiratory syncytial virus infection does not decrease viral load or severity of illness", Pediatr Infect Dis J. Jul. 2014;33(7):703-9. doi: 10.1097/INF.0000000000000240.

Respaud, et al., "Development of a drug delivery system for efficient alveolar delivery of a neutralizing monoclonal antibody to treat pulmonary intoxication to ricin", J Control Release. Jul. 28, 2016;234:21-32. doi: 10.1016/j.jconrel.2016.05.018. Epub May 9, 2016.

Rezaee, et al., "Ongoing developments in RSV prophylaxis: a clinician's analysis", Curr Opin Virol. Jun. 2017;24:70-78. doi: 10.1016/j.coviro.2017.03.015. Epub May 10, 2017.

Robinson, J.A., "Max Bergmann lecture protein epitope mimetics in the age of structural vaccinology", J Pept Sci. Mar. 2013;19(3):127-40. doi: 10.1002/psc.2482. Epub Jan. 24, 2013.

Sanders and Ponzio, "Vectored immunoprophylaxis: an emerging adjunct to traditional vaccination", Trop Dis Travel Med Vaccines. Feb. 10, 2017;3:3. doi: 10.1186/s40794-017-0046-0. eCollection 2017.

Scheltema, et al., Respiratory syncytial virus prevention and asthma in healthy preterm infants: a randomised controlled trial, Lancet Respir Med. Apr. 2018;6(4):257-264. doi: 10.1016/S2213-2600(18)30055-9. Epub Feb. 27, 2018.

Shah, et al., "Immunodeficiency scoring index to predict poor outcomes in hematopoietic cell transplant recipients with RSV infections", Blood. May 22, 2014;123(21):3263-8. doi: 10.1182/ blood-2013-12-541359. Epub Apr. 3, 2014.

Simoes, et al., "Past, Present and Future Approaches to the Prevention and Treatment of Respiratory Syncytial Virus Infection in Children", Infect Dis Ther. Mar. 2018;7(1):87-120. doi: 10.1007/ s40121-018-0188-z. Epub Feb. 22, 2018.

Stobart, et al., "A live RSV vaccine with engineered thermostability is immunogenic in cotton rats despite high attenuation", Nat Commun. Dec. 21, 2016;7:13916. doi: 10.1038/ncomms13916.

Tabrizi, et al., "Biodistribution mechanisms of therapeutic monoclonal antibodies in health and disease", AAPS J. Mar. 2010; 12(1):33-43. doi: 10.1208/s12248-009-9157-5. Epub Nov. 19, 2009.

Tripp, et al., "CX3C chemokine mimicry by respiratory syncytial virus G glycoprotein", Nat Immunol. Aug. 2001;2(8):732-8. doi: 10.1038/90675.

Tripp, et al., "Respiratory Syncytial Virus: Targeting the G Protein Provides a New Approach for an Old Problem", J Virol. Jan. 17, 2018;92(3):e01302-17. doi: 10.1128/JVI.01302-17. Print Feb. 1, 2018.

Villenave, et al., "In vitro modeling of respiratory syncytial virus infection of pediatric bronchial epithelium, the primary target of infection in vivo", Proc Natl Acad Sci U S A. Mar. 27, 2012;109(13):5040-5. doi: 10.1073/pnas.1110203109. Epub Mar. 12, 2012.

Wessler, et al., "Using Computational Modeling to Optimize the Design of Antibodies That Trap Viruses in Mucus", ACS Infect Dis. Jan. 8, 2016;2(1):82-92. doi: 10.1021/acsinfecdis.5b00108. Epub Oct. 17, 2015.

Wright, et al., "Growth of respiratory syncytial virus in primary epithelial cells from the human respiratory tract", J Virol. Jul. 2005;79(13):8651-4. doi: 10.1128/JVI.79.13.8651-8654.2005.

Wu, et al., "An analysis of the sequences of the variable regions of Bence Jones proteins and myeloma light chains and their implications for antibody complementarity", J Exp Med. Aug. 1, 1970;132(2):211-50. doi: 10.1084/jem.132.2.211.

Yamazaki, et al., "Neutralizing Anti-Hemagglutinin Monoclonal Antibodies Induced by Gene-Based Transfer Have Prophylactic and Therapeutic Effects on Influenza Virus Infection", Vaccines (Basel). Jun. 26, 2018;6(3):35. doi: 10.3390/vaccines6030035.

Yu, et al., "Molecular Selection, Modification and Development of Therapeutic Oligonucleotide Aptamers", Int J Mol Sci. Mar. 11, 2016;17(3):358. doi: 10.3390/ijms17030358.

Zhang, et al., "Respiratory syncytial virus infection of human airway epithelial cells is polarized, specific to ciliated cells, and without obvious cytopathology", J Virol. Jun. 2002;76(11):5654-66. doi: 10.1128/jvi.76.11.5654-5666.2002.

Zhu, et al., "Analysis of respiratory syncytial virus preclinical and clinical variants resistant to neutralization by monoclonal antibodies palivizumab and/or motavizumab", J Infect Dis. Mar. 1, 2011;203(5):674-82. doi: 10.1093/infdis/jiq100. Epub Jan. 5, 2011.

Lenci, Elena, and Andrea Trabocchi. "Peptidomimetic toolbox for drug discovery." Chemical Society Reviews 49.11 (2020): 3262-3277.

Products for Nebulization—Characterization Tests, USP Pharmacopeial Forum, vol. 36(2) p. 534-539, Mar.-Apr. 2010.

\* cited by examiner

SEQUENCE LISTING

```
<160> NUMBER OF SEQ ID NOS: 29

<210> SEQ ID NO 1
<211> LENGTH: 127
<212> TYPE: PRT
<213> ORGANISM: Homo sapiens
<220> FEATURE:
<221> NAME/KEY: CHAIN
<222> LOCATION: (1)..(127)
<223> OTHER INFORMATION: heavy chain of respiratory syncytial virus
      antibody 1F12
```

<400> SEQUENCE: 1

Gln Val Gln Leu Val Gln Ser Glu Ser Glu Val Lys Lys Pro Gly Ala
1               5                   10                  15

Ser Val Thr Val Ser Cys Lys Pro Ser Gly Tyr Thr Phe Asn Thr Tyr
            20                  25                  30

Tyr Ile His Trp Val Arg Gln Ala Pro Gly Gln Gly Leu Glu Trp Met
        35                  40                  45

Gly Val Ile Asn Pro Ser Gly Ser Thr Thr Tyr Thr Gln Arg Phe
    50                  55                  60

Gln Asp Arg Val Thr Met Thr Thr Asp Thr Ser Thr Asn Thr Ile Tyr
65                  70                  75                  80

Met Asp Leu Thr Ser Leu Arg Ser Asp Thr Ala Met Tyr Tyr Cys
                85                  90                  95

Val Arg Gly Ser Asn Leu Leu Pro His Leu Trp Glu Trp Lys Pro Ser
                100                 105                 110

His Phe Asp Ser Trp Gly Gln Gly Thr Leu Val Thr Val Ser Ser
            115                 120                 125

<210> SEQ ID NO 2
<211> LENGTH: 126
<212> TYPE: PRT
<213> ORGANISM: Homo sapiens
<220> FEATURE:
<221> NAME/KEY: CHAIN
<222> LOCATION: (1)..(126)
<223> OTHER INFORMATION: heavy chain of respiratory syncytial virus
      antibody 3G12

<400> SEQUENCE: 2

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Asn Tyr Tyr Trp Gly Trp Ile Arg Gln Pro Pro Gly Lys Gly Leu Glu
        35                  40                  45

Trp Ile Ala Ser Ile His Asp Ser Gly Ser Ile Tyr Tyr Asn Pro Ser
    50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg His Leu Val Trp Phe Gly Glu Leu Arg Asn Asn Trp Phe
                100                 105                 110

Asp Pro Trp Gly Gln Gly Thr Leu Val Thr Val Ala Ser Ala
            115                 120                 125

<210> SEQ ID NO 3
<211> LENGTH: 124
<212> TYPE: PRT
<213> ORGANISM: Homo sapiens
<220> FEATURE:
<221> NAME/KEY: CHAIN
<222> LOCATION: (1)..(124)
<223> OTHER INFORMATION: heavy chain of respiratory syncytial virus
      antibody 1A5

<400> SEQUENCE: 3

Gln Leu Gln Leu Gln Glu Ser Gly Pro Gly Leu Val Lys Pro Ser Glu
1               5                   10                  15

```
Thr Leu Ser Leu Thr Cys Thr Val Ser Gly Asp Ser Ile Thr Ser Gly
            20                  25                  30

Gln Tyr Tyr Trp Ala Trp Ile Arg Gln Ala Pro Gly Lys Gly Leu Glu
            35                  40                  45

Trp Ile Gly Ser Ile His Tyr Ser Gly Ser Thr Tyr Gln Asn Pro Ser
    50                  55                  60

Leu Lys Ser Arg Leu Thr Ile Ser Val Asp Thr Ser Arg Asp Gln Ile
65                  70                  75                  80

Ser Met Lys Leu Ser Ser Val Thr Val Ala Glu Ser Ala Val Tyr Tyr
                85                  90                  95

Cys Ala Arg Gln Gln Leu Ser Leu Ser Pro Val Glu Asn Trp Phe Asp
            100                 105                 110

Pro Trp Gly Gln Gly Thr Leu Val Thr Val Ser Ser
            115                 120
```

<210> SEQ ID NO 4
<211> LENGTH: 124
<212> TYPE: PRT
<213> ORGANISM: Homo sapiens
<220> FEATURE:
<221> NAME/KEY: CHAIN
<222> LOCATION: (1)..(124)
<223> OTHER INFORMATION: heavy chain of respiratory syncytial virus antibody 3D3

<400> SEQUENCE: 4

```
Glu Glu Gln Leu Val Glu Ser Gly Gly Gly Leu Val Gln Pro Gly Arg
1               5                   10                  15

Ser Leu Arg Leu Ser Cys Val Gly Ser Gly Leu Arg Phe Glu Glu His
            20                  25                  30

Ala Met His Trp Val Arg Gln Ala Pro Gly Arg Gly Leu Glu Trp Val
            35                  40                  45

Ser Gly Ile Ser Trp Asn Ser Gly Ser Val Gly Tyr Ala Asp Ser Val
    50                  55                  60

Lys Gly Arg Phe Thr Thr Ser Arg Asp Asn Ala Lys Asp Ile Leu Phe
65                  70                  75                  80

Leu Glu Met Asn Thr Leu Arg Ser Glu Asp Thr Ala Leu Tyr Phe Cys
                85                  90                  95

Ala Ile Met Val Ala Thr Thr Lys Asn Asp Phe His Tyr Tyr Lys Asp
            100                 105                 110

Val Trp Gly Lys Gly Thr Thr Val Thr Val Ser Ser
            115                 120
```

<210> SEQ ID NO 5
<211> LENGTH: 124
<212> TYPE: PRT
<213> ORGANISM: Homo sapiens
<220> FEATURE:
<221> NAME/KEY: CHAIN
<222> LOCATION: (1)..(124)
<223> OTHER INFORMATION: heavy chain of respiratory syncytial virus antibody 1G1

<400> SEQUENCE: 5

```
Gln Val His Leu Val Gln Ser Gly Val Glu Val Lys Lys Pro Gly Ala
1               5                   10                  15

Ser Val Arg Val Ser Cys Lys Ala Ser Gly Tyr Thr Phe Ala Thr Tyr
            20                  25                  30

Gly Ile Thr Trp Val Arg Gln Ala Pro Gly Arg Gly Leu Glu Trp Val
```

```
                35                  40                  45
Gly Trp Ile Thr Pro Tyr Asn Asp Arg Thr Ser Tyr Ala Gln Ile Phe
        50                  55                  60

His Gly Arg Val Thr Met Thr Thr Asp Thr Ser Thr Asn Thr Ala Tyr
65                  70                  75                  80

Met Glu Leu Arg Ser Leu Arg Ser Asp Asp Thr Ala Met Tyr Tyr Cys
                85                  90                  95

Ala Arg Asn His Cys Asn Phe Tyr His Asp Phe Trp Ser Gly Leu Asp
            100                 105                 110

Tyr Trp Gly Gln Gly Thr Leu Val Ser Val Ser Ser
        115                 120

<210> SEQ ID NO 6
<211> LENGTH: 121
<212> TYPE: PRT
<213> ORGANISM: Homo sapiens
<220> FEATURE:
<221> NAME/KEY: CHAIN
<222> LOCATION: (1)..(121)
<223> OTHER INFORMATION: heavy chain of respiratory syncytial virus
      antibody 2B11

<400> SEQUENCE: 6

Gln Val Gln Leu Val Gln Ser Gly Ala Glu Val Lys Lys Pro Gly Ser
1               5                   10                  15

Ser Val Lys Val Pro Cys Lys Ala Ser Gly Gly Thr Phe Ser Thr Tyr
                20                  25                  30

Pro Ile Ser Trp Val Arg Gln Ala Pro Gly Gln Gly Leu Glu Trp Met
            35                  40                  45

Gly Arg Ile Ile Pro Asp Pro Pro Met Ala Asn Ile Ala Gln Lys Phe
        50                  55                  60

Gln Gly Arg Val Ser Phe Ser Ala Asp Lys Ser Thr Thr Ile Val Tyr
65                  70                  75                  80

Met Glu Leu Ser Ser Leu Arg Ser Glu Asp Thr Ala Val Tyr Phe Cys
                85                  90                  95

Ala Arg Glu Ile Leu Gln Ser Pro Pro Phe Ala Val Asp Val Trp Gly
            100                 105                 110

Gln Gly Thr Met Val Ala Val Ser Ser
        115                 120

<210> SEQ ID NO 7
<211> LENGTH: 127
<212> TYPE: PRT
<213> ORGANISM: Homo sapiens
<220> FEATURE:
<221> NAME/KEY: CHAIN
<222> LOCATION: (1)..(127)
<223> OTHER INFORMATION: heavy chain of respiratory syncytial virus
      antibody 5D8

<400> SEQUENCE: 7

Gln Ala Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Tyr Ser
                20                  25                  30

Gly Met His Trp Val Arg Gln Ala Pro Gly Arg Gly Leu Glu Trp Leu
            35                  40                  45

Ala Val Ile Ser Tyr Asp Gly Asn Lys Met Tyr Tyr Ala Asp Ser Val
        50                  55                  60
```

```
Lys Gly Arg Phe Thr Ile Ser Arg Asp Asn Ser Lys Met Thr Leu Tyr
 65                  70                  75                  80

Leu Gln Met Asn Ser Leu Arg Arg Glu Asp Thr Ala Val Tyr Tyr Cys
                 85                  90                  95

Ala Lys Asp Gly Leu Asp Tyr Gly Gly Asp Leu Val Tyr Tyr Gly Met
            100                 105                 110

Asp Val Trp Gly Asn Gly Thr Thr Val Thr Val Ser Ser Ala Ser
            115                 120                 125
```

```
<210> SEQ ID NO 8
<211> LENGTH: 126
<212> TYPE: PRT
<213> ORGANISM: Homo sapiens
<220> FEATURE:
<221> NAME/KEY: CHAIN
<222> LOCATION: (1)..(126)
<223> OTHER INFORMATION: heavy chain of respiratory syncytial virus
      antibody 2D10

<400> SEQUENCE: 8

Gln Val Gln Leu Val Gln Ser Gly Pro Glu Val Lys Lys Pro Gly Ala
  1               5                  10                  15

Ser Val Arg Leu Ser Cys Lys Ala Ser Gly Tyr Val Phe Thr Asn Tyr
             20                  25                  30

Gly Val Ser Trp Val Arg Gln Ala Pro Gly Gln Gly Leu Glu Trp Met
         35                  40                  45

Gly Trp Ser Ser Pro Tyr Asn Gly Asn Thr Tyr Tyr Ala Gln Lys Leu
     50                  55                  60

Lys Ala Arg Val Thr Met Thr Thr Asp Thr Ser Thr Asn Thr Ala Tyr
 65                  70                  75                  80

Met Glu Leu Arg Ser Leu Arg Ser Asp Asp Thr Ala Val Tyr Tyr Cys
                 85                  90                  95

Gly Arg Asp Met Leu Gly Val Val Gln Ala Val Ala Gly Pro Phe Asp
            100                 105                 110

Ser Trp Gly Gln Gly Thr Leu Val Thr Val Ser Ser Ala Ser
            115                 120                 125
```

```
<210> SEQ ID NO 9
<211> LENGTH: 126
<212> TYPE: PRT
<213> ORGANISM: Homo sapiens
<220> FEATURE:
<221> NAME/KEY: CHAIN
<222> LOCATION: (1)..(126)
<223> OTHER INFORMATION: heavy chain of respiratory syncytial virus
      antibody 3F9

<400> SEQUENCE: 9

Gln Val Gln Leu Val Gln Ser Gly Gly Glu Val Lys Arg Pro Gly Ala
  1               5                  10                  15

Ser Val Arg Val Ser Cys Lys Ala Ser Gly Tyr Thr Phe Ile Asn Tyr
             20                  25                  30

Ala Ile Ser Trp Val Arg Gln Ala Pro Gly Gln Gly Leu Glu Trp Leu
         35                  40                  45

Gly Trp Ile Ser Ala Tyr Asn Gly Asn Thr His Tyr Ala Gln Lys Val
     50                  55                  60

Gln Asp Arg Val Thr Met Thr Thr Asp Ala Ser Thr Thr Ala Tyr
 65                  70                  75                  80

Met Glu Leu Arg Gly Leu Lys Ser Asp Asp Thr Ala Val Tyr Ser Cys
                 85                  90                  95
```

Ala Arg Leu Pro Leu Leu Gly Tyr Ser Ser Gly Trp Tyr Ala Phe Asp
            100                 105                 110

Met Trp Arg Gln Gly Thr Met Val Pro Val Ser Ser Ala Ser
            115                 120                 125

<210> SEQ ID NO 10
<211> LENGTH: 127
<212> TYPE: PRT
<213> ORGANISM: Homo sapiens
<220> FEATURE:
<221> NAME/KEY: CHAIN
<222> LOCATION: (1)..(127)
<223> OTHER INFORMATION: heavy chain of respiratory syncytial virus
      antibody 1D4

<400> SEQUENCE: 10

Gln Val Gln Leu Leu Gln Ser Gly Ala Glu Leu Lys Lys Pro Gly Ala
1               5                   10                  15

Ser Val Lys Val Ser Cys Gln Ala Ser Ile Asp Thr Phe Ser Thr Tyr
            20                  25                  30

Tyr Ile His Trp Val Arg Gln Ala Pro Gly Gln Gly Leu Glu Trp Leu
        35                  40                  45

Gly Val Ile Asn Pro Ser Gly Gly Ser Thr Thr Tyr Ala Gln Lys Phe
    50                  55                  60

Gln Asp Arg Ile Thr Leu Thr Thr Asp Thr Ser Thr Arg Thr Val Tyr
65                  70                  75                  80

Met Asp Leu Ser Ser Leu Arg Ser Glu Asp Thr Ala Val Tyr Tyr Cys
                85                  90                  95

Ala Arg Val His Lys Gly Arg Ala Glu Gln Trp Gln Leu Leu His Gly
            100                 105                 110

His Phe Asp Leu Trp Gly Arg Gly Ser Leu Val Thr Val Ser Ser
        115                 120                 125

<210> SEQ ID NO 11
<211> LENGTH: 126
<212> TYPE: PRT
<213> ORGANISM: Homo sapiens
<220> FEATURE:
<221> NAME/KEY: CHAIN
<222> LOCATION: (1)..(126)
<223> OTHER INFORMATION: heavy chain of respiratory syncytial virus
      antibody 1G8

<400> SEQUENCE: 11

Gln Leu Gln Leu Gln Glu Ser Gly Pro Gly Leu Val Lys Pro Ser Glu
1               5                   10                  15

Thr Leu Ser Leu Thr Cys Thr Val Ser Gly Asp Ser Ile Thr Ser Gly
            20                  25                  30

Gln Tyr Tyr Trp Ala Trp Ile Arg Gln Ala Pro Gly Lys Gly Leu Glu
        35                  40                  45

Trp Ile Gly Ser Ile His Tyr Ser Gly Ser Thr Tyr Gln Asn Pro Ser
    50                  55                  60

Leu Lys Ser Arg Leu Thr Ile Ser Val Asp Thr Ser Arg Asp Gln Ile
65                  70                  75                  80

Ser Met Lys Leu Ser Ser Val Thr Val Ala Glu Ser Ala Val Tyr Tyr
                85                  90                  95

Cys Ala Lys Gln Gln Leu Ser Leu Ser Pro Val Glu Asn Trp Phe Asp
            100                 105                 110

Pro Trp Gly Gln Gly Thr Leu Val Thr Val Ser Ser Ala Ser
        115                 120                 125

```
            115                 120                 125

<210> SEQ ID NO 12
<211> LENGTH: 120
<212> TYPE: PRT
<213> ORGANISM: Homo sapiens
<220> FEATURE:
<221> NAME/KEY: CHAIN
<222> LOCATION: (1)..(120)
<223> OTHER INFORMATION: heavy chain of respiratory syncytial virus
      antibody 6A12

<400> SEQUENCE: 12

Glu Val Gln Val Val Glu Ser Gly Gly Gly Leu Val Gln Pro Gly Gly
1               5                   10                  15

Ser Leu Arg Leu Ser Cys Val Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Tyr Ser Asp Gly Ser Ser Thr Thr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Val Arg Val Leu Gly Ala Ala Met Phe Asp Ile Trp Gly Gln Gly Thr
            100                 105                 110

Val Val Thr Val Ser Ser Ala Ser
        115                 120

<210> SEQ ID NO 13
<211> LENGTH: 128
<212> TYPE: PRT
<213> ORGANISM: Homo sapiens
<220> FEATURE:
<221> NAME/KEY: CHAIN
<222> LOCATION: (1)..(128)
<223> OTHER INFORMATION: heavy chain of respiratory syncytial virus
      antibody 10C6

<400> SEQUENCE: 13

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Gly Tyr
            20                  25                  30

Ala Met His Trp Val Arg Gln Ala Pro Ala Lys Gly Leu Glu Trp Val
        35                  40                  45

Ala Val Ile Ser Phe Asp Gly Ser Asn Asn Tyr Tyr Ala Asp Ser Val
    50                  55                  60

Lys Gly Arg Phe Thr Ile Ser Arg Asp Asn Ser Lys Asn Met Leu Phe
65                  70                  75                  80

Leu Gln Met Asn Ser Leu Arg Ala Glu Asp Thr Ala Val Tyr Tyr Cys
                85                  90                  95

Val Arg Pro Asp Val Ile Ala Val Ala Gly Thr Ala Leu Ser Asn Pro
            100                 105                 110

Phe Asp Leu Trp Gly Leu Gly Thr Met Val Thr Val Ser Ser Ala Ser
        115                 120                 125

<210> SEQ ID NO 14
<211> LENGTH: 122
```

```
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)..(122)
<223> OTHER INFORMATION: humanized heavy chain of respiratory syncytial
      virus antibody Hu 131-2G

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Gly Phe
            20                  25                  30

Thr Met Asn Trp Val Arg Gln Ala Thr Gly Gln Gly Leu Glu Trp Met
        35                  40                  45

Gly Leu Ile Asn Pro Phe Asn Gly Asn Thr Gly Tyr Asn Gln Lys Phe
    50                  55                  60

Lys Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Lys Ser Tyr Asp Tyr Glu Ala Trp Phe Thr Tyr Trp
            100                 105                 110

Gly Gln Gly Thr Leu Val Thr Val Ser Ala
        115                 120

<210> SEQ ID NO 15
<211> LENGTH: 109
<212> TYPE: PRT
<213> ORGANISM: Homo sapiens
<220> FEATURE:
<221> NAME/KEY: CHAIN
<222> LOCATION: (1)..(109)
<223> OTHER INFORMATION: light chain of respiratory syncytial virus
      antibody 1E12

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Asn Asn
            20                  25                  30

Tyr Leu Ala Trp Tyr Gln Gln Lys Pro Gly Gln Ala Pro Arg Leu Leu
        35                  40                  45

Ile Tyr Asp Ser Phe Ser Arg Ala Thr Gly Ile Pro Glu Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Tyr Val Arg Ser Pro
                85                  90                  95

Leu Thr Phe Gly Pro Gly Thr Lys Val Glu Ile Lys Arg
            100                 105

<210> SEQ ID NO 16
<211> LENGTH: 107
<212> TYPE: PRT
<213> ORGANISM: Homo sapiens
<220> FEATURE:
<221> NAME/KEY: CHAIN
<222> LOCATION: (1)..(107)
<223> OTHER INFORMATION: light chain of respiratory syncytial virus
``` antibody 3G12

<400> SEQUENCE: 16

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asn Ser Asn
            20                  25                  30

Leu Ala Trp Tyr Gln His Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Phe Gly Pro Gly Thr Lys Val Asp Leu Lys Arg
            100                 105

<210> SEQ ID NO 17
<211> LENGTH: 109
<212> TYPE: PRT
<213> ORGANISM: Homo sapiens
<220> FEATURE:
<221> NAME/KEY: CHAIN
<222> LOCATION: (1)..(109)
<223> OTHER INFORMATION: light chain of respiratory syncytial virus
      antibody 1A5

<400> SEQUENCE: 17

Glu Ile Val Val Thr Gln Ser Pro Val Thr Leu Ser Val Ser Pro Gly
1               5                   10                  15

Glu Ser Ala Thr Leu Ser Cys Arg Ser Ala Arg Ser Val Gly Ser Arg
            20                  25                  30

Leu Ala Trp Tyr Gln Gln Lys Pro Gly Gln Pro Pro Arg Leu Leu Ile
        35                  40                  45

Phe Ala Ala Ser Thr Arg Ala Thr Gly Ile Pro Ala Arg Phe Ser Gly
    50                  55                  60

Ser Gly Ser Gly Thr Asp Phe Thr Leu Ile Ile Ser Gly Leu Gln Ser
65                  70                  75                  80

Glu Asp Tyr Ala Val Tyr Tyr Cys Gln Gln Tyr Lys Glu Trp Pro Leu
                85                  90                  95

Phe Thr Phe Gly Pro Gly Thr Thr Val Asp Ser Lys Arg
            100                 105

<210> SEQ ID NO 18
<211> LENGTH: 106
<212> TYPE: PRT
<213> ORGANISM: Homo sapiens
<220> FEATURE:
<221> NAME/KEY: CHAIN
<222> LOCATION: (1)..(106)
<223> OTHER INFORMATION: light chain of respiratory syncytial virus
      antibody 3D3

<400> SEQUENCE: 18

Gln Ile Val Leu Thr Gln Ser Pro Ala Thr Leu Ser Leu Ser Pro Gly
1               5                   10                  15

Glu Arg Ala Thr Leu Ser Cys Lys Ala Ser Gln Ser Val Ser Asn His
            20                  25                  30

Leu Ala Trp Tyr Gln Gln Lys Pro Gly Gln Ala Pro Arg Leu Leu Ile

```
                35                  40                  45
Tyr Glu Thr Ser Asn Arg Ala Thr Gly Ile Pro Pro Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Asn Asn Trp Tyr Thr
                 85                  90                  95

Phe Gly Gln Gly Thr Lys Leu Glu Ile Lys
            100                 105

<210> SEQ ID NO 19
<211> LENGTH: 108
<212> TYPE: PRT
<213> ORGANISM: Homo sapiens
<220> FEATURE:
<221> NAME/KEY: CHAIN
<222> LOCATION: (1)..(108)
<223> OTHER INFORMATION: light chain of respiratory syncytial virus
      antibody 1G1

<400> SEQUENCE: 19

Ser Phe Glu Leu Thr Gln Pro Pro Ser Val Ser Val Ser Pro Gly Gln
 1               5                  10                  15

Thr Ala Arg Ile Thr Cys Ser Gly Asp Ala Leu Pro Lys Gln Tyr Val
                 20                  25                  30

Tyr Trp Tyr Gln Gln Lys Pro Gly Gln Ala Pro Val Leu Val Ile Tyr
            35                  40                  45

Lys Thr Thr Glu Arg Pro Ser Gly Ile Pro Glu Arg Phe Ser Asp Ser
 50                  55                  60

Ser Ser Gly Thr Thr Val Thr Leu Thr Ile Ser Ala Ala Gln Ala Glu
 65                  70                  75                  80

Asp Glu Ala Asp Tyr Tyr Cys Gln Ser Val Asp Ser Ser Gly Thr Tyr
                 85                  90                  95

Val Phe Gly Ile Gly Thr Lys Val Thr Val Leu Gly
            100                 105

<210> SEQ ID NO 20
<211> LENGTH: 113
<212> TYPE: PRT
<213> ORGANISM: Homo sapiens
<220> FEATURE:
<221> NAME/KEY: CHAIN
<222> LOCATION: (1)..(113)
<223> OTHER INFORMATION: light chain of respiratory syncytial virus
      antibody 2B11

<400> SEQUENCE: 20

Gln Ser Ala Leu Thr Gln Pro Ala Ser Val Ser Gly Ser Pro Gly Gln
 1               5                  10                  15

Ser Ile Thr Ile Ser Cys Thr Gly Ser Ser Ser Asp Val Gly Gly Tyr
                 20                  25                  30

Ser His Val Ser Trp Tyr Gln Gln His Pro Gly Lys Val Pro Lys Leu
            35                  40                  45

Ile Ile Ser Glu Val Ser Asn Arg Pro Ser Gly Ile Ser Asn Arg Phe
 50                  55                  60

Ser Gly Ser Lys Ser Ala Asn Thr Ala Ser Leu Thr Ile Ser Gly Leu
 65                  70                  75                  80

Gln Pro Glu Asp Glu Ala Asp Tyr Tyr Cys Gly Ser Tyr Ala Ser Thr
                 85                  90                  95
```

```
Asn Ile Leu His Tyr Val Phe Gly Thr Gly Thr Lys Val Thr Val Leu
            100                 105                 110

Ser

<210> SEQ ID NO 21
<211> LENGTH: 114
<212> TYPE: PRT
<213> ORGANISM: Homo sapiens
<220> FEATURE:
<221> NAME/KEY: CHAIN
<222> LOCATION: (1)..(114)
<223> OTHER INFORMATION: light chain of respiratory syncytial virus
      antibody 5D8

<400> SEQUENCE: 21

Ser Tyr Glu Leu Thr Gln Pro Pro Ser Val Ser Val Ser Pro Gly Gln
1               5                   10                  15

Thr Gly Arg Ile Thr Cys Thr Gly Ser Glu Ala Ser Gly Asp Ala Leu
            20                  25                  30

Ala Ser Arg Tyr Ala Tyr Trp Tyr Gln His Lys Ser Gly Gln Ala Pro
        35                  40                  45

Val Val Leu Ile Tyr Lys Asp Thr Glu Arg Pro Ser Gly Ile Ser Glu
    50                  55                  60

Arg Phe Ser Gly Ser Ser Ser Gly Thr Thr Val Thr Leu Ile Ile Ser
65                  70                  75                  80

Gly Val Leu Ala Glu Asp Glu Ala Asp Tyr Tyr Cys Lys Thr Ser Val
                85                  90                  95

Arg Asn Gly Thr Ser Trp Val Phe Gly Thr Gly Thr Met Leu Thr Val
            100                 105                 110

Leu Arg

<210> SEQ ID NO 22
<211> LENGTH: 108
<212> TYPE: PRT
<213> ORGANISM: Homo sapiens
<220> FEATURE:
<221> NAME/KEY: CHAIN
<222> LOCATION: (1)..(108)
<223> OTHER INFORMATION: light chain of respiratory syncytial virus
      antibody 2D10

<400> SEQUENCE: 22

Asp Thr Pro Met Thr Gln Ser Pro Ser Ser Val Ser Ala Ser Val Gly
1               5                   10                  15

Asp Arg Val Thr Ile Ser Cys Arg Ala Ser Gln Gly Ile Ser Asn Ser
            20                  25                  30

Leu Ala Trp Tyr Gln Gln Lys Leu Gly Lys Ala Pro Gln Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Thr Phe Pro Phe
                85                  90                  95

Thr Phe Gly Pro Gly Thr Lys Val Glu Val Arg Arg
            100                 105

<210> SEQ ID NO 23
<211> LENGTH: 111
<212> TYPE: PRT
```

```
<213> ORGANISM: Homo sapiens
<220> FEATURE:
<221> NAME/KEY: CHAIN
<222> LOCATION: (1)..(111)
<223> OTHER INFORMATION: light chain of respiratory syncytial virus
      antibody 3F9

<400> SEQUENCE: 23

Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Asn Lys Arg Pro Ser Gly Val Pro Asp Arg Phe
    50                  55                  60

Ser Gly Ser Lys Ser Gly Asn Thr Ala Ser Leu Thr Val Ser Gly Leu
65                  70                  75                  80

Gln Ala Glu Asp Glu Ala Glu Tyr Tyr Cys Ser Ser Tyr Ala Gly Ser
                85                  90                  95

Met Asn Trp Val Phe Gly Gly Gly Thr Lys Leu Thr Val Leu Gly
            100                 105                 110

<210> SEQ ID NO 24
<211> LENGTH: 114
<212> TYPE: PRT
<213> ORGANISM: Homo sapiens
<220> FEATURE:
<221> NAME/KEY: CHAIN
<222> LOCATION: (1)..(114)
<223> OTHER INFORMATION: light chain of respiratory syncytial virus
      antibody 1D4

<400> SEQUENCE: 24

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Thr Tyr Leu Ala Trp Tyr Gln Gln Lys Pro Arg Gln
        35                  40                  45

Pro Pro Glu Leu Leu Ile Tyr Trp Ala Ser Thr Arg Glu Ser Gly Val
    50                  55                  60

Pro Asp Arg Phe Ser Gly Ser Gly Ser Gly Thr Asn Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Tyr Thr Phe Gly Gln Gly Thr Lys Leu Glu Ile
            100                 105                 110

Lys Arg

<210> SEQ ID NO 25
<211> LENGTH: 109
<212> TYPE: PRT
<213> ORGANISM: Homo sapiens
<220> FEATURE:
<221> NAME/KEY: CHAIN
<222> LOCATION: (1)..(109)
<223> OTHER INFORMATION: light chain of respiratory syncytial virus
      antibody 1G8

<400> SEQUENCE: 25
```

```
Glu Ile Val Val Thr Gln Ser Pro Val Thr Leu Ser Val Ser Pro Gly
1               5                   10                  15

Glu Ser Ala Ala Leu Ser Cys Arg Ala Ser Arg Ser Val Gly Ser Arg
            20                  25                  30

Leu Ala Trp Tyr Gln Gln Lys Pro Gly Gln Pro Pro Arg Leu Leu Ile
        35                  40                  45

Phe Ala Ala Ser Thr Arg Ala Thr Gly Ile Pro Ala Arg Phe Ser Gly
50                  55                  60

Ser Gly Ser Gly Thr Asp Phe Thr Leu Ile Ile Ser Gly Leu Gln Ser
65                  70                  75                  80

Glu Asp Tyr Ala Val Tyr Tyr Cys Gln Gln Tyr Lys Glu Trp Pro Leu
                85                  90                  95

Phe Thr Phe Gly Pro Gly Thr Thr Val Asp Ser Lys Arg
            100                 105
```

<210> SEQ ID NO 26
<211> LENGTH: 110
<212> TYPE: PRT
<213> ORGANISM: Homo sapiens
<220> FEATURE:
<221> NAME/KEY: CHAIN
<222> LOCATION: (1)..(110)
<223> OTHER INFORMATION: light chain of respiratory syncytial virus
      antibody 6A12

<400> SEQUENCE: 26

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Ser Asp Ala Ser Asn Arg Ala Thr Gly Ile Pro Pro Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Arg Phe Thr Phe Gly Pro Gly Thr Ile Val Asp Ile Arg Arg
            100                 105                 110
```

<210> SEQ ID NO 27
<211> LENGTH: 107
<212> TYPE: PRT
<213> ORGANISM: Homo sapiens
<220> FEATURE:
<221> NAME/KEY: CHAIN
<222> LOCATION: (1)..(107)
<223> OTHER INFORMATION: light chain of respiratory syncytial virus
      antibody 10C6

<400> SEQUENCE: 27

```
Glu Ile Val Met Thr Gln Ser Pro Ala Thr Leu Ser Val Ser Pro Gly
1               5                   10                  15

Glu Arg Ala Leu Ser Cys Arg Ala Ser Gln Ser Val Arg Ser Asn Leu
            20                  25                  30

Val Trp Tyr Gln Gln Lys Pro Gly Gln Ala Pro Arg Leu Leu Ile Phe
        35                  40                  45

Gly Ala Ser Thr Arg Ala Thr Gly Ile Pro Ala Arg Phe Ser Gly Ser
50                  55                  60
```

```
Gly Ser Gly Thr Glu Phe Thr Leu Thr Ile Ser Ser Leu Gln Ser Glu
 65                  70                  75                  80

Asp Phe Ala Leu Tyr Phe Cys Gln Gln Asn Asn Asn Trp Pro Pro Thr
                 85                  90                  95

Phe Gly Gln Gly Thr Arg Leu Glu Ile Lys Arg
            100                 105

<210> SEQ ID NO 28
<211> LENGTH: 113
<212> TYPE: PRT
<213> ORGANISM: Artificial Sequence
<220> FEATURE:
<223> OTHER INFORMATION: synthetic construct
<220> FEATURE:
<221> NAME/KEY: CHAIN
<222> LOCATION: (1)..(113)
<223> OTHER INFORMATION: humanized light chain of respiratory syncytial
      virus antibody Hu 131-2G

<400> SEQUENCE: 28

Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Thr Ile Val His Thr
                 20                  25                  30

Asn Gly Asn Thr Tyr Leu Glu Trp Tyr Leu Gln Lys Pro Gly Gln Ser
             35                  40                  45

Pro Gln Leu Leu Ile Tyr Lys Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Val Pro Phe Thr Phe Gly Ser Gly Thr Lys Leu Glu Ile Lys
            100                 105                 110

Arg

<210> SEQ ID NO 29
<211> LENGTH: 18
<212> TYPE: PRT
<213> ORGANISM: Artificial Sequence
<220> FEATURE:
<223> OTHER INFORMATION: Synthetic

<400> SEQUENCE: 29

Gly Gly Gly Gly Ser Gly Gly Gly Gly Ser Gly Gly Gly Gly Ser Gly
 1               5                  10                  15

Gly Gly
```

IMMUNOGEN PROVIDING AN EXTENDED PROTECTIVE LIFETIME AGAINST RESPIRATORY SYNCYTIAL VIRUS (RSV) AND VACCINES THEREOF

CROSS-REFERENCE TO RELATED APPLICATIONS

This application is a continuation of, and claims the benefit under 35 U.S.C. § 120 to, International Application No. PCT/US2019/045775, filed Aug. 8, 2019, and now expired which claims priority to U.S. provisional application 62/716,184 filed 8 Aug. 2018, the contents of which are incorporated herein by reference in its entirety.

INCORPORATION BY REFERENCE OF SEQUENCE LISTING

The present application is being filed along with a Sequence Listing in electronic format. The Sequence Listing is provided as an ST.25 file entitled 12774-138US1_SeqList_October_2024, which was created Oct. 21, 2024 and is 36,864 bytes_in size. The information in the electronic format of the Sequence Listing is incorporated by reference in its entirety.

FIELD OF THE INVENTION

The invention is directed to improved methods and materials for prophylaxis and treatment of respiratory syncytial virus (RSV) infection.

BACKGROUND ART

RSV is a negative-strand RNA virus with 10 genes encoding 11 proteins, which has resisted effective management for over 60 years in part because infection does not provide robust immunity (Broadbent, L. et al. *Influenza Other Respir Viruses* (2015) 9:169-78). To date, no vaccine has been approved despite several substantial attempts (Jorquera, P. A. and Tripp, R. A. *Expert Rev Respir Med* (2017) 11 (8): 609-615). Over 50% of infants in the US are infected during their first year, with nearly 5% requiring hospitalization (American Academy of Pediatrics Committee on Infectious Diseases, American Academy of Pediatrics Bronchiolitis Guidelines. *Pediatrics* (2014) 134: e620-38). Severe RSV disease in infancy is an established risk factor for childhood asthma-like symptoms (Gelfand, E. W. *Curr Opin Immunol* (2012) 24 (6): 713-9). Preterm infants (<29 weeks gestational age) who are at particularly high risk have been the focus for prophylaxis with a humanized mouse monoclonal antibody or mAb (palivizumab, marketed by MedImmune as SynagisR), an expensive treatment which reduces morbidity but not mortality (Meissner, H. C. and Kimberlin, D. W. *Pediatrics* (2013) 132:915-8). Global incidence of RSV infection in young children is less well documented than in the US but is believed to be more than double that of US, with higher mortality rates (Nair H., et al. *Lancer* (2010) 375 (9725): 1545-1555). In addition, up to 12% of medically attended acute respiratory illness in older adults is attributed to RSV infection with 6-8% of these cases being lethal. Hospitalizations last 3 to 6 days, with a substantial fraction admitted to the intensive care unit (Colosia, A. D., et al. *PLOS ONE*. (2017) 12 (8): @0182321). RSV infections are also common in immunocompromised patients, with mortality of over 25% (Shah. D. P., et al. *Blood* (2014) 123 (21): 3263-3268).

Two subtypes of RSV, A and B, circulate as the predominant strains alternately at ~1-2-year intervals, with comparable incidence worldwide. The two subtypes comprise different genotypes, and can co-circulate during an infection. Thus, an effective vaccine or treatment needs to show activity on strains from both subtypes.

RSV has two major surface glycoproteins, F and G. Currently, the sole marketed mAb against RSV is palivizumab (commercially available under the brand name SynagisR) which is only approved for prophylactic use in premature infants, and is directed against the F protein. This mAb is broadly useful due to conservation of the F protein sequence among strains, although escape mutations are readily detected (Zhu, Q., et al. *J Infect Dis* (2011) 203:674-82). Efforts to develop a vaccine based on the RSV F protein have been described (Jorquera, P. A. and Tripp. R. A. *Expert Rev Respir Med* (2017) 11 (8): 609-615). Although antibody titers to the F protein produced in immunized subjects have reached levels that inhibit RSV propagation in cell culture, RSV disease has not been sufficiently prevented for any such vaccine to receive FDA approval.

Further, palivizumab treatment of premature infants (born at 32-35 weeks gestation) did not have a major effect on asthma or lung function at age 6 years (Scheltema, N. M., et al. *Lancet Respir. Med*. (2018) 6:257-264). Escape mutations from palivizumab are well documented and may contribute to the lack of efficacy (Bates, J. T., et al. *Virology* (2014) 454-455:139-44). Moreover, a higher affinity derivative of palivizumab, motavizumab, failed to show a clinical benefit as a treatment of acute infection in full term infants, even when given at the very high dose (for a mAb) of 100 mg/kg (Ramilo O., et al. *Pediatr Infect Dis J*. (2014) 33 (7): 703-9).

By contrast, the G protein overall is quite variable among strains. However, a region in the middle of the sequence including residues 167-176 is very highly conserved, and is denoted as the central conserved domain (CCD). In fact, <1% of ~7,000 published RSV sequences show any changes in the CCD, with the majority being conservative substitutions.

Initial attempts at prophylaxis for RSV by vaccination with formalin-inactivated virus proved counterproductive, leading to enhanced disease and pulmonary eosinophilia (Kim. H. W., et al. *Am J Epidemiol* (1969) 89:422-434). This harmful reaction now appears to result from an interaction of RSV G protein with the CX3CR1 receptor, resulting in recruitment and possible activation of inflammatory cells. The region that interacts with this receptor, the CX3C motif is at positions 182-186, just outside the CCD. As a result of this observation the formalin inactivated vaccine has not been further developed. Moreover. RSV G protein has been shown to exacerbate RSV infection by depressing the interferon response (Oshansky. C. M. et al. *Viral Immunol* (2009) 22 (3): 147-161). Vaccines based on variants of RSV G protein but lacking the CX3CR1 interaction have been proposed. U.S. Pat. No. 8,173,131 discloses vaccines wherein the CX3C motif is modified or compositions that comprise antibodies or other moieties that prevent interaction of the motif with the receptor, thus preventing cell entry. U.S. Pat. No. 8,846,056 discloses immunogenic peptides from RSV G protein as vaccine components, specifically including residues 164-176 or 155-206. U.S. Pat. No. 9,321, 830 discloses mAbs useful in treating or preventing RSV infections that bind to conserved linear sequences of the G protein of RSV in the region including residues 167-176; as these antibodies were derived from the natural human immune repertoire, they are expected to be minimally immunogenic when administered to a human subject.

About 15% of the RSV G protein is secreted due to use of an alternative translation start site at codon 48 that eliminates the cytoplasmic domain and a portion of the transmembrane domain region (Hendricks. D. A., et al. *J Virol* (1988) 62:2228-33). Deletion of this start site considerably reduces virulence (Stobart. C. C., et al. *Nat Commun* (2016) 7:13916). (Arnold. R., et al *Virology* (2004) 330: 384-397). Such an attenuated live virus may be useful as a vaccine, although the high transmissibility of RSV poses a substantial risk of transfer to people at risk for severe disease despite the attenuation, including the very young, the elderly, and the immunocompromised. The secreted G protein poses an additional obstacle to an effective vaccine or treatment, because high affinity for antigen is needed for neutralizing soluble factors; otherwise the mAb simply provides a circulating reservoir for the antigen, extending its serum half-life and distributing it more efficiently around the body (Tabrizi, M. et al. *AAPS J* (2010) 12:33-43). As a result, mAbs with low picomolar (pM) affinity for the RSV G protein CCD, such as those disclosed in U.S. Pat. No. 9,321,830 are generally advantageous.

Collarini, E. J. et al. *J Immunol* (2009) 183:6338-45 describes high affinity, broadly neutralizing mAbs that bind to the RSV G protein CCD as well as antibodies with varying affinities including 3D3 (1.1 pM). 2B11 (10 pM), 3G12 (580 pM). 5D8 (4.4 nM). The mAb 3D3 has shown broad neutralizing activity both in vitro and in rodent models: the epitope for 3D3 defined at the level of short linear peptides is highly conserved across nearly all circulating strains. An additional mAb, 2D10, is of interest, because no linear peptide epitope could be defined for it although it is active in viral neutralization assays in vitro, albeit with lower potency than 3D3 (U.S. Pat. No. 8,273, 354). Additional native human mAbs with affinities in the low nM to high pM range are disclosed in U.S. Pat. No. 10,035,842.

As disclosed in US Publication No. US-2019-0135876-A1, the structures of peptides from the CCD of the G protein complexed with mAbs 3D3 and 2D10 have been determined at high resolution by x-ray crystallography and the conformational character of the epitopes thereby defined.

A recombinant fusion protein comprising the central region (residues 131-230)) of the G proteins of both RSV A and B subtypes was shown to be an effective immunogen in mice (Lee, J. Y. and Chang, J. *PLOS One* (2017) 12: e0175384). A G protein peptide, residues 148-198 emulsified in DMSO and PBS, has also been tested in mice as an immunogen and found to be effective at inducing antibodies that both neutralize infection and block G protein binding to CX3CR1 (Choi, Y., et al. *Viral Immunol* (2012) 25 (3): 193-203). Similarly, vaccination with nanonparticles that incorporate the G protein residues 169-198 induced protection in mice challenged with RSV (Jorquera, P. A., et al. *PLOS One* (2013) 8: e74905). Fine scale optimization of peptides from this region has also been attempted, with insertion of one extra residue into the G protein at residues 182-186 greatly reducing the deleterious effects of G protein on the host immune response (Boyoglu-Barnum, S., et al. *J Virol* (2017) 91 (10) pii: e02059-16) but likely also reducing the ability to induce mAbs against the native CCD.

The contents of these documents and all documents cited herein are incorporated herein by reference.

Although the results to date are encouraging, no RSV G protein vaccine has been approved. Repeated infection is common for this virus, unlike many others, with increased severity in many instances. Criteria defining quality of an immunogen, for which further improvements are useful, include: duration of response: uniformity of response (titer and affinity) across a diverse human population: broad spectrum (active against all circulating strains): safety (in particular, lack of deleterious pharmacological activity on the CX3C chemokine receptor); and stability (particularly important for use in countries lacking an effective refrigerated supply chain). Prevention of viral disease by vaccination usually involves subdermal or intramuscular injection of either intact virus particles, disabled virus particles, or some portion of a virus particle combined with additional components called adjuvants. Adjuvants are added to vaccines for the purposes of enhancing vaccine efficacy, stability, and preservation. Antibodies may be administered intravenously, intramuscularly, or by inhalation.

Use of immune complexes as vaccines can enhance the primary immune response (both kinetically and quantitatively) compared to vaccination with antigen alone (Houston W E, et al. *Journal of Infectious Diseases* (1977) 135 (4): 600-10), (Brady, L. J. *Infection and Immunity* (2005) 73 (2): 671-8). This is attributed to increased efficiency in antigen processing and presentation (Abdel-Motal. U. M., Wigglesworth. K, Galili, U. *Vaccine* (2009) 27 (23): 3072-82). Inclusion of anti-antigen antibody complex in vaccines has been found in other systems to boost vaccine effectiveness by stimulating formation of immune complexes which in turn stimulate antigen-specific immune responses (Lambour, J. et al. *Emerging Microbes & Infections* (2016) 5: e92: doi: 10.1038/emi.2016.97).

Improvements in key features of both active and passive vaccines targeting the G protein is the focus of the present invention. Although efforts with regard to RSV immunization have focused on the F protein, it is now understood that the G protein is an important target and it can be effectively adopted as an immunogen for improved RSV prophylaxis.

DISCLOSURE OF THE INVENTION

In one aspect, the present invention enables the conserved CCD of the RSV G protein to elicit neutralizing antibodies in a subject while eliminating the undesired interaction of the CX3C motif with its receptor. This is accomplished by mutating the G protein to prevent this interaction or by providing antibodies or other moieties that compete with the G protein for this receptor. According to the present invention, an anti-G mAb is used to bind RSV G protein in a vaccine composition. The antibodies employed in the complexes of the present invention prevent the interaction of the RSV G protein with the host cell receptor CX3CR1, thereby preventing adverse events tied to that biological activity, without interfering with the ability of the G protein or the CCD portion thereof to induce neutralizing antibodies. Such a combination has been shown to block the activation of the CX3CR1-receptor (see Example 4 below), and such complexes are able to increase efficiency of immune response as explained below.

Thus, in one aspect, the invention relates to an immunogen and vaccine compositions that contain it that comprise RSV G protein or a fragment comprising the CCD, or a homolog or stabilized forms thereof or peptidomimetic of either, complexed with a mAb (or fragments or derivative thereof) that binds to RSV G protein with high affinity and prevents interaction with CX3CR1. The immunogen may be administered along with a vaccine adjuvant. The CCD is that of residues 131-230 or 167-176 of a G protein. To be effective in this aspect, the mAb needs to have high enough affinity to support formation of stable immune complexes, such as an affinity equal to or better than that associated with a Kd of 100 pM or 50 pM or 25 pM or less.

In another aspect, the invention includes methods to provide prophylaxis with respect to RSV infection in a subject which method comprises administering to a subject in need of such treatment a pharmaceutical or veterinary composition including these immunogens.

In another aspect, the invention includes sequence modifications to a mAb against the CCD of the RSV G protein wherein the modifications result in extended serum half-life. Technology for achieving this goal has long been known, as described in U.S. Pat. No. 8,318,907. Targeting the G protein in this fashion is a contribution to passive immunotherapy/prophylaxis against RSV, wherein the selection of antigen to target is important. That is, the vast majority of vaccine/antibody efforts on RSV have been focused on the F protein, with no prior suggestion that the long half-life approach currently being applied to the F protein should or could be applied to the G protein. Other techniques for extending the half-life include fusion to an albumin binding domain or modification of the Fc region to enhance binding to mucin.

In yet another aspect, the invention includes expression in the cells of a subject of the mAb by Vectored Immunoprophylaxis (VIP), also referred to as Immunoprophylaxis by Gene Trasfer (IGT) or Vector-Mediated Antibody Gene transfer, which comprises introducing genes encoding a mAb into the subject's cells which then secrete the mAb (Sanders, J. W. and Ponzio, T. A. *Tropical Diseases, Travel Medicine and Vaccines* (2017) 3:3).

In another aspect, the invention includes formulation of a mAb against the CCD of RSV G protein that enables delivery by inhalation. Suitable technology to achieve this goal is described in U.S. Pat. No. 9,718,875. A review of suitable nebulizers is: (Ari, A. and Fink, J. B. *Curr Pharm Biotechnol.* (2016) 17 (14): 1268-1277).

MODES OF CARRYING OUT THE INVENTION

The conformational epitopes on RSV G CCD defined by high affinity, broadly neutralizing mAbs 3D3 and 2B10 disclosed in U.S. Pat. No. 8,273,354, incorporated herein by reference include helices, disulfide bonds, and polar and hydrophobic interactions between discontinuous amino acids. Similar results have been described using additional mAbs against the G CCD (Jones H. G., et al. *PLOS Pathog* (2018) 14 (3): e1006935). These features may explain why linear RSV G epitope peptides have not been fully effective as antigens: for example, an early attempt to target the CCD of the G protein with a recombinant protein vaccine (BBG2Na) showed only a moderate ability to induce neutralizing antibodies in healthy, young adults and a more recent effort also using recombinant G protein failed to establish efficacy in elderly adults (Rezaee, F., et al. *Curr Opin Virol* (2017) 24:70-78).

As described in Publication No. US-2019-0135876-A1 these conformational features can be stabilized by use of chemical crosslinkers or non-natural amino acids (Robinson, J. A. *J Pept Sci* (2013) 19 (3): 127-40). The contact residues with the efficacious mAbs comprise most of the CCD but not all. Mutations in the residues not involved in mAb binding may thus be mutated to prevent interaction of the immunogen with CX3CR1 without affecting the mAb binding, or as employed in the present invention the site responsible for binding CX3CR1 can be masked by binding to an mAb or fragment thereof (such as those noted above) so as to prevent interaction with this receptor. This is an advantage over and above the enhanced immunogenicity of the complex described for such complexed immunogens.

Definitions

Unless defined otherwise, all technical and scientific terms used herein have the same meanings as commonly understood by one of ordinary skill in the art to which this disclosure belongs. Detailed methods for constructing many of the reagents is provided in Example 1 herein below.

"Protein", "peptide" and "polypeptide" are used interchangeably and to refer to chains of naturally occurring amino acids coupled through amide bonds such that they can be synthesized by recombinant methods regardless of the length of the chain. "Homologs" are peptides or proteins with similar sequences, but alterations such that the homolog is 80% or 85% or 95% or 99% homologous to the referent. "Peptidomimetics" have similar homologies but include unnatural or synthetic amino acids, including D and L isomers and amino acid analogs linked by amide linkages or other bonds, e.g., ester, ether, etc. "Peptidomimetics" also include organic molecules not obviously analogous to peptides, including, for example, aptamers. As defined herein, based on previous studies, the CCD of the G protein is that portion of the protein represented by residues 169-198.

As used herein, "subject" refers to a human or non-human animal, including laboratory models for RSV such as rodents, or to livestock or pets.

As used herein, "binding moiety" includes antibodies and alternative non-immunoglobulin binding moieties as set forth hereinbelow. "Antibodies" include immunoreactive fragments of traditional antibodies and their various fragmented forms that still retain immunospecificity such as Fab. F(ab') 2. Fv fragments, single-chain antibodies in which the variable regions of heavy and light chain are directly bound without some or all of the constant regions. Since light chains are often interchangeable without destroying specificity, antibodies composed of a heavy chain variable region that determines the specificity of the antibody may be combined with a heterologous light chain variable region. Chimeric antibodies with constant and variable regions derived, for example, from different species are also included. Also included are antibodies in which the Fc portion of the molecule has been mutated to enhance or reduce binding to Fc receptors (Kontermann. R. E. *BioDrugs* (2009) 23 (2): 93-109).

For the variable regions of mAbs, as is well known, the critical amino acid sequences are the complementarity-determining region (CDR) sequences arranged on a framework, which framework can vary without necessarily affecting specificity or decreasing affinity to an unacceptable level. Definition of these CDR regions is accomplished by art-known methods. Specifically, the most commonly used method for identifying the relevant CDR regions is that of Kabat as disclosed in Wu. T. T., et al., *J. Exp. Med.* (1970) 132: 211-250 and in the book Kabat. E. A., et al. (1983) Sequence of Proteins of Immunological Interest. Bethesda National Institute of Health. 323 pages. Another similar and commonly employed method is that of Chothia (Chothia. C., et al., *J. Mol. Biol.* (1987) 196: 901-917) and (Chothia, C. et al., *Nature* (1989) 342: 877-883), including additional modifications (Abhinandan, K. R., et al., *Mol. Immunol.* (2008) 45: 3832-3839), The mAbs described herein include the CDR regions as defined by any of these systems or other recognized systems known in the art.

The specificities of the binding of mAbs are defined, as noted, by the CDR regions mostly those of the heavy chain, but complemented by those of the light chain as well (the light chains being somewhat interchangeable). Therefore, the mAbs of the invention may contain the three CDR regions of a heavy chain and optionally the three CDR's of a light chain that matches it. Because binding affinity is also determined by the manner in which the CDR's are arranged on a framework, the mAbs may contain complete variable regions of the heavy chain containing the three relevant CDR's as well as, optionally, the complete light chain variable region comprising the three CDR's associated with the light chain complementing the heavy chain in question. Preferred CDR's for the mAbs of the present invention are disclosed in FIGS. 5A and 5B of U.S. Pat. No. 8,273,354. In particular, mAbs of the invention may include variable regions of the heavy and light chains of mAb 3G12, 3D3, 2B11, or 2D10, i.e., SEQ ID NO: 2 and 16: SEQ ID NO: 4 and 18: SEQ ID NO: 6 and 20; SEQ ID NO: 8 and 22, respectively.

The invention also includes binding moieties that mimic the binding characteristics of mAbs. Suitable mAb mimics include aptamers (Yu, Y., et al. *Int J Mol Sci* (2016) 17 (3): 358) and protein mimics of antibodies or fragments thereof (alternative scaffolds) such as camelids, anticalins, ankyrin repeat proteins (Azhar A., et al. *Int J Biol Macromol* (2017) 102:630-641).

An alternative to active immunization is to provide a mAb as passive immunotherapy, either prophylactically or therapeutically. For prophylaxis, it is useful to modify the Fc region of the mAb to extend serum half-life as has been described for an anti-F protein mAb now in clinical development (U.S. Pat. No. 7,323,172). For therapeutic use, an inhaled formulation is useful, as has been described for mAbs against influenza (U.S. Pat. No. 9,718,875).

Recombinant Aspects

Any proteins or peptides of the invention including antibodies or antigen binding fragments thereof may be produced recombinantly using known techniques. The invention also includes nucleic acid molecules comprising nucleotide sequences encoding them, as well as vectors or expression systems that comprise these nucleotide sequences, cells containing expression systems or vectors for expression of these nucleotide sequences and methods to produce the peptides by culturing these cells and recovering the binding moieties produced. Any type of cell typically used in recombinant methods can be employed including prokaryotes, yeast, mammalian cells, insect cells and plant cells. Also included are human cells (e.g., muscle cells or lymphocytes) transformed with one or more recombinant molecules that encode the relevant peptides.

Activities Based on the CX3C Chemokine Motif

Although variable overall, RSV G (298 residues) contains an approximately 40 amino acid central conserved domain (CCD) that is highly conserved, and devoid of glycosylation: this portion of the protein has been shown to play key roles in both virus infection and viral pathogenesis. Specifically, RSV G CCD contains a CX3C chemokine motif that facilitates binding to the human chemokine receptor CX3CR1 to promote RSV infection in human airway epithelial cells as well as modulating signaling that affects trafficking of $CX3CR1^+$ immune cells resulting in airway congestion (Tripp, R. A., et al. *J Virol* (2018) 92: e01302-17).

Aside from the presence of a CX3C motif and its two disulfide bonds there are no structural or sequence similarities between RSV G and fractalkine/CX3CL1, the only known ligand for CX3CR1. This structural divergence despite similar functionality provides an opportunity to develop therapies that selectively block the viral-host interaction, a strategy that led to an antagonist of the HIV co-receptor CCR5 (Lieberman-Blum, S. S., et al. *Clinical Therapeutics* (2008) 30:1228-1250).

The affinity of the stabilized forms of RSV G protein CCD or peptidomimetics thereof and their spatially constrained forms can be tested using the ELISA assays described in Example 2 or using one of the many alternative methods known in the art. Assays for induction of efficacious antibodies can be tested, using the assays set forth in Example 3 herein below; or other suitable tests well known to one of ordinary skill in the art of vaccines. The ability to activate or inhibit the CX3C receptor can be assessed using, for example, the chemotaxis assay set forth in Example 4 herein below or any other suitable method, such as a calcium flux assay that has shown good correlation with chemotaxis in a study of mutants of the endogenous ligand for CX3CR1 (fractalkine) (Dorgham, K. et al. *J Leukoc Biol* (2009) 86 (4): 903-11).

Immunogens

Three design goals dominate optimization of a G protein immunogen.

First, the pharmacological activity of the G protein is deleterious in the context of RSV infection and it is thus preferable to minimize that activity in the immunogen either by modification of the immunogen structure as previously described or by masking that site as disclosed herein.

Second, high affinity antibodies are needed to neutralize the deleterious soluble G protein produced by virus infected cells, and therefore antibodies generated by the immunogens preferably have these properties. The method of the present invention maximizes the likelihood of achieving this goal by minimizing alterations to the native structure. Optimization of the ratio of mAb to antigen in an immunogen complex is also useful, because an excess of mAb discourages formation of immune complexes and thus reduces the efficacy of the mAb-antigen complex as an immunogen (Manca, F., et al. *J Experimental Medicine* (1991) 173 (1): 37-48).

Third, since RSV is an important pathogen worldwide, including in countries that lack a refrigerated supply chain for delivery of vaccines, stabilization of the immunogen to allow transport and storage at room temperature (or above) is also desirable. Formalin inactivation of live virus, which is effective in other vaccines, is not acceptable for RSV since the first such vaccine caused disease exacerbation upon subsequent natural infection (Kim, H. W., et al. *Am J Epidemiol* (1969) 89:422-34).

With respect to this third aspect, conformational stability achieved by stabilization of the structure using mutations chosen based on antibody-antigen high resolution structural data, can result in higher titer more uniformly across immunized subjects than for the parental virus, as shown for the RSV F protein (Mcclellan, J. S., et al. *Science* (2013) 340 (6136): 1113-1117). The natural G protein CCD is poorly immunogenic, and thus modifications to improve immunogenicity are important. Since the G protein CCD can be made either synthetically or recombinantly, methods well known in the art can be used to systematically mutate this peptide. To facilitate evaluation of a large number of such variants, in vitro assays are needed. Assays for thermal stability known in the literature include observation of increased fluorescence of a dye when bound to hydrophobic sites exposed as the protein unfolds (Biggar, K. K., et al. *BioTechniques* (2012) 53:231-238) and observation of secondary structure character by circular dichroism (Kelly, S. M. and Price, N. C. *Biochim Biophys Acta* (1997) 1338 (2): 161-185).

In addition to the disadvantage of requiring refrigeration, the use of flexible peptides as immunogens often elicits antibodies that bind weakly (>micromolar Kd) to conformational epitopes in folded proteins. For that reason, conformationally constrained synthetic epitope mimetics are of particular interest in immunogen design, with examples including efforts addressing HIV, hepatitis C, influenza, and others (Robinson, J. A. *J Pept Sci* (2013) 19 (3): 127-40).

Peptides incorporating non-natural motifs are often quite resistant to proteolytic degradation, which is an advantageous feature unrelated to the mimicry itself. A disadvantage of small molecules ("haptens") is that they are often not immunogenic themselves: however, they can become effective immunogens when presented to the immune system embedded in virus like particles (Buonaguro, L., et al. *Exp. Rev. Vaccines* (2011) 10:1569-1583).

In particular, the F protein of RSV has been subjected to such mimicry. In this instance, two "staples" (crosslinks) were required to create an effective mimic, which displayed nanomolar potency for competitive inhibition of RSV infection in Hep-2 cells in vitro (Gaillard, V., et al. *Antimicrob Agents Chemother*. (2017) 61 (4) pii: e02241-16).

Extended mAb Dosing

Still another aspect of the invention is providing a passive vaccine wherein an antibody directed to the RSV G protein is modified to provide an extended time period of effective lifetime in a subject or wherein the lifetime is extended by conjugation to albumin or wherein the antibody or antigen binding portion is expressed in the cells of the subject.

RSV is a seasonal virus, with a typical season lasting from October to April in the US. Over that time period, among children younger than 5 years old, there are 2.1 million outpatient visits and 57,527 hospitalizations (Hall, C. B., et al. *New Engl J Med*. (2009) 360 (6): 588-98). For adults older than 65 years, there are 177,000 hospitalizations and 14,000 deaths (Falsey, A. R., et al. *New Engl J Med*. (2005) 352 (17): 1749-59). The advantage of an extended half-life antibody for RSV to provide protection throughout the season is thus well recognized in the field.

In one embodiment, the Fc region of the mAb is modified to enhance the binding of the Fc region of IgG1 to the neonatal Fc receptor (FcRn). An Fc modified mAb against the RSV F protein (MEDI8897) is in clinical development by Sanofi in partnership with AstraZeneca (Medimmune) (ClinicalTrials.gov Identifier: NCT02290340). This mAb has 100-fold higher potency in vitro as compared to the only approved mAb targeting RSV (palivizumab). The mAb has been engineered with a triple-amino-acid (M252Y/S254T/T256E [YTE]) substitution within its Fc region (Griffin, M. P., et al. *Antimicrob Agents Chemother*. (2017) 61 (3): e01714-16). The YTE substitution enhances the binding of IgG1 to the FcRn under the acidic conditions (pH 6.0) of the lysosome. This prevents degradation and increases recirculation to the surface of the cell, thereby prolonging the serum half-life of the antibody. The combination of higher potency and longer half-life enables a single dose to provide neutralizing activity for 3-4 months. While precedent supports the expectation of utility for an extended half-life mAb, the natural history of RSV in infants includes a rebound in viral load (of 2-3 logs) about 2 weeks post-infection, which occurs in about one third of infants (Brint, M. E. et al. *Pediatr Res* (2017) 82 (5): 872-880). This result is thought to reflect escape from the initial natural antibody response to the virus. Accordingly, for an extended half-life mAb to be maximally effective, it needs to target a functionally critical site on the virus structure. Antibodies targeting the RSV G protein, and in particular the CCD of the G protein, meet this criterion far better than antibodies targeting the F protein. Thus, the YTE substitution is applied to the mAb of the invention, such as 3G12, 3D3, 2B11 and 2D10 to provide more effective neutralization of the virus.

In another embodiment, the Fc region of the mAb is modified to bind to mucus components. Thus is of particular utility for inhaled formulations (Wessler, T., et al. *ACS Infect. Dis*. (2016) 2 (1): 82-92). Another option for extending the half-life of a mAb or fragment thereof is to fuse or conjugate the sequence to an albumin binding domain (Malm, M., et al. *Biotechnol J*. (2014) 9 (9): 1215-22).

In still another option the mAb or antigen binding portion is expressed in the cells of the subject by Vectored Immunoprophylaxis, a process in which genes encoding previously characterized neutralizing antibodies are vectored into the subject's cells which then secrete the monoclonal antibodies encoded by those genes. The technology has been proven effective in animals and is under consideration for providing extended protection in people against HIV (Sanders, J. W. and Ponzio, T. A. *Tropical Diseases, Travel Medicine and Vaccines* (2017) 3:3).

In one implementation, a vector comprising self-complementary adeno-associated virus (scAAV) of serotype 8 (low incidence of antibody response) supported long-lived expression of full-length human antibodies driven from CMV promoters after administration through a single injection of the gastrocnemius muscle. Within one week, antibody gene expression was detectable, achieving maximum levels after 12-16 weeks and then decreasing two- to three-fold before stabilizing for the duration of the 64-week study at >50 μg/mL of mAb. When this system was used to express a broadly neutralizing HIV antibody, mice were protected from repeated HIV infection by both IV and vaginal exposure routes for at least 15 weeks (Balazs, A. B., et al. *Nature* (2012) 481 (7379): 81-84; Balazs, A. B. et al. *Nature Medicine* (2014) 20 (3): 296-300).

In another implementation, a plasmid encoding the genes for the heavy and light chain of an antibody was introduced by electroporation into mouse muscle pre-treated with hyaluronidase to improve plasmid access to the cells (Yamazaki, T., et al. *Vaccines* (2018) 6 (3): 35). Plasmid vectors are considered to be safer than AAV, are easy to prepare and stable during storage. Moreover, plasmid DNA does not induce an immune response against itself. An antibody against the HA protein of influenza induced by this means in mice produced >10 μg/mL of the antibodies in serum for at least 70 days following antibody gene transfer, significantly higher than the level of HA-specific IgG antibody induced from vaccination (1-3 μg/mL).

Inhaled Formulation

The only approved antiviral drug for RSV, ribavirin, is rarely used due to its toxicity and weak efficacy (Simoes, E. A. F., et al. *Infect Dis Ther*. (2018) 7 (1): 87-120). Accordingly, palliative care, notably including mechanical ventilation, is a common technique for managing severe RSV disease in both infants and the elderly. Incorporating an antiviral antibody into the treatment by inhaled delivery is thus compatible with standard care. Commercially available mesh nebulizers are suitable for generating droplets containing antibody in the size range (low micrometer diameter) appropriate for distribution throughout the lung (Respaud. R., et al. *J Control Release* (2016) 234:21-32). The reduced dose for comparable efficacy as compared to systemically delivered antibody is particularly advantageous for treating the elderly due to the >10-fold higher systemic dose required for adults as compared to infants.

The RSV G protein CCD binding to CX3CR1 has been established as the dominant route of infection in human airway epithelial cells (Jeong, K. I., et al. *PLOS One* (2015) 10: e0130517; Johnson, S. M., et al. *PLOS Pathog* (2015) 11: e100531). Accordingly, delivery of the mAb to the airways will provide direct neutralization of virus shed into the airways from the apical surface of the infected cells (Villenave, R., et al. *Proc. Natl Acad Sci USA* (2012) 109:5040-5045: Wright, P. F., et al., *J Virol* (2005) 79:8651-8654: Zhang. L. et al., *J Virol* (2002) 76:5654-5666). Systemically delivered antibody, by contrast, attacks the basolateral side of the cells and is thus less efficient for neutralizing the virus. An inhaled antibody mimic ("nanobody" derived from a camelid antibody) targeting the RSV F protein has been tested clinically (Gottlieb, J., et al. *J Heart Lung Transplant* (2016) 35:213-221). The longer half-life of a full IgG is advantageous compared to this precedent.

US/EU Pharm Chapter 1601 for Nebulizer Product Using Tidal Breathing provides regulatory guidance to qualify the delivered dose (USP Pharmacopeial Forum 36 (2): 534). A marketed nebulizer, the AeroNeb-Solo R; device from Aerogen, Ltd (Deerfield, IL) uses a highly efficient vibrating mesh to generate the aerosol. Piezoelectric energy applied to the vibrational element at 150 MHz causes vibration of each of 1000 microscopic funnel shaped apertures within the mesh to act as a micropump drawing liquid through the holes producing a low velocity aerosol optimized for targeted drug delivery to the lungs. The low velocity minimizes shear forces that can denature proteins, making this system particularly useful for delivery of antibody therapeutics. The device typically delivers 9 times more aerosol dose than a standard small volume nebuliser such as a pressurized metered dose inhaler (as is typical for asthma treatment). Aerosol particle size is measured using a cascade impactor (In-Tox Products, Moriarity, NM). Using this system, we have produced aerosols of an antibody with a 2.17 μm mass median aerodynamic diameter (MMAD) and a 2.24 μm geometric standard deviation (GSD).

A second generation Aerogen product is specifically designed to treat patients requiring a ventilator. This Photo Defined Aperture Plate (PDAP) device provides significant improvements in ease of use as well as further dose reduction over the first generation product by achieving tighter control over the mean particle size. This is important because aerosol droplets that are too large do not penetrate deeply into the lungs, but if the droplets are too small, they don't settle out and are simply exhaled. The PDAP device also allows the nebulizer to be synchronized with the patient's breathing. Only generating the aerosol during the inspiration phase of the breathing cycle substantially improves the fraction of drug that is deposited in the lungs.

Applications

The invention is also directed to pharmaceutical and veterinary compositions which comprise as active ingredients the binding moieties, mutants or other peptides or peptidomimetics of the invention. The compositions contain suitable physiologically compatible excipients such as buffers and other simple excipients. The compositions may include additional active ingredients as well, in particular in the case of immunogens immune system stimulants as vaccine adjuvants. The pharmaceutical or veterinary compositions may also contain other formulation excipients, including formulations for intra-nasal or inhaled delivery of mAbs as described in U.S. Pat. No. 9,718,875.

The immunogens are employed in a method to generate an immune response to RSV, comprising administering formulations containing them to a subject, including a human subject, such as a pregnant woman, an infant, an elderly human, or an immunocompromised subject. Infections related to RSV in other animal species may also be treated prophylactically by the immunogens or binding moieties of the invention.

EXAMPLE 1: PRODUCTION OF PROTEINS

A. Production of Fab 3D3 and ScFv 2D10

Recombinant mAbs 3D3 and 2D10 were produced by transient-transfection in CHO cells and purification by immobilized protein A.

The Fab fragment of 3D3 was generated from recombinantly produced 3D3 by incubation with immobilized papain, followed by removal of the Fc fragment with immobilized protein A. Fab 3D3 was then purified by Superdex™ 200 size-exclusion chromatography media in 10 mM Tris-HCl pH 8.0 and 150 mM NaCl.

For recombinant scFv 2D10, a synthetic gene codon-optimized for *Drosophila melanogaster* encoding 2D10 heavy chain variable region, a (GGGGS): GGG linker (SEQ ID NO: 29), and 2D10 light chain variable region, was cloned into pMT-puro in-frame with an N-terminal BiP signal sequence and a C-terminal thrombin cleavage site followed by a Twin-Strep™ purification tag. The resulting scFv 2D10 expression plasmid was used to obtain stably-transfected Schneider 2 (S2) insect cells. Secreted scFv 2D10 was affinity purified on a StrepTrap™ column (biotin binding chromatography media), digested with thrombin protease to remove the purification tag, and then purified by Superdex™ 200 size-exclusion chromatography in 10 mM Tris-HCl pH 8.0 and 150 mM NaCl.

B. Production of Epitopes

A synthetic gene encoding RSV G ectodomain (G[ecto]) P03423) was cloned into pCF in-frame with an N-terminal TPA signal sequence and C-terminal tandem 6-histidine and Twin-Strep™ purification tags. G[ecto] was produced by transient-transfection in CHO cells and secreted G[ecto| was affinity purified on a StrepTrap™ column.

A synthetic gene codon-optimized for *Escherichia coli* encoding RSV G residues 161 to 197 (G [161-197]) with a C-terminal 6-histidine purification tag was cloned into pET52b. The peptide was expressed overnight in *E. coli* BL21 (DE3) at 18° C. The cells were then were lysed by ultrasonication in 20 mM Tris-HCl pH 8.0, 150 mM NaCl. and 25 mM imidazole (Buffer A) containing 2 μM $MgCl_2$, benzonase, and protease inhibitors. RSV G [161-197] was purified from soluble lysates by HisTrap™ FF affinity chromatography and eluted with a gradient into Buffer B (Buffer A containing 500 mM imidazole). Analogous methods were used to produce related peptides (G [162-172] and G[169-198]).

EXAMPLE 2: ELISA ASSAYS

Purified mAbs at a concentration of 5 μg/mL (150) μL total) are incubated overnight at room temperature in 96-well ELISA microtiter plates. Plates are then washed three times with PBS containing 0.05% Tween 20 (PBST). Wells are blocked by adding 150 μL of 5% BSA in PBS and incubating at room temperature for 1 hr followed by three PBST washes. Recombinant RSV G[ecto] at 5 μg/mL or RSV G[161-197] at 20 μg/mL in 1% BSA in PBS is serially diluted 1:3 with 1% BSA in PBS. Wells are incubated with 150 μL RSV G protein for 1 hr at room temperature, plates washed three times with PBST, and then incubated for 1 hr at room temperature with 150 µL HRP-conjugated-HisProbe (ThermoFisher Scientific) diluted 1:5000 in 1% BSA in PBS. Plates are washed three times with PBST and developed by adding peroxidase substrate o-phenylenediamine dihydrochloride (OPD) in 0.05 M phosphate-citrate buffer pH 5.0 and 1.5% hydrogen peroxide for 10 min at room temperature. The reactions are stopped by incubation with 2N sulfuric acid for 10 min at room temperature, and the absorbance measured at 490 nm. ELISA experiments are performed in biological triplicates.

EXAMPLE 3: TESTS FOR EFFICACY OF IMMUNOGENS

Efficacy can be evaluated by injecting mice with a vaccine comprising RSV G or fragments thereof, an anti-G mAb that blocks the interaction of the G protein with CX3CR1, along with standard vaccine adjuvants; alternatively, administration may be by intra-nasal route (Kruijsen, D., et al. *J Virol* (2013) 87 (13): 7550-57). After adequate time for immunization, the mice are challenged with a virulent strain of RSV and observed for morbidity and mortality. The composition of the present invention results in protection of the subject mice. The immunogens of the invention are evaluated in a murine model using the following criteria.

TABLE 1

Immunogen Efficacy Criteria

| Category | Score | Detailed Criteria |
|---|---|---|
| RSV titers in lungs: | 4 | no detectable RSV |
| Based on pfu/g lung tissue at day 5 post-challenge and RT-PCR quantitation of viral genomes/g tissue | 3 | 75% reduction of RSV in lungs vs. naïve mice |
| | 2 | 50% reduction of RSV in lungs vs. naïve mice |
| | 1 | 25% reduction of RSV in lungs vs. naïve mice |
| Lung Pathology: | 4 | No pathology |
| Based on the mean score for each parameter, i.e. peribronchiolar, perivascular, interstitial and alveolar that involve each lung section evaluated | 3 | slight |
| | 2 | moderate |
| | 1 | severe |
| Duration of immunity: | 3 | >6 months |
| Based on full protection from subsequent virus challenge | 2 | 1-6 months |
| | 1 | <1 month |
| Weight loss: | 3 | No weight loss |
| Parameter of morbidity | 2 | 5-19% weight loss |
| | 1 | ≥20% weight loss |
| Cellular immunity: | 3 | robust; Th1/Th2 balanced |
| Th1/Th2 assayed by IFNγ and IL-4 ELISPOTs or by intracellular cytokine FACS and by ELISA of bronchial alveolar lavage fluid from the lungs | 2 | moderate; Th1/Th2 balanced |
| | 1 | Unbalanced Th2/Th1 |

EXAMPLE 4: CHEMOTAXIS ASSAY

An in vitro assay for RSV G modulation of CX3CR1 measures receptor-mediated chemotaxis of human monocyte THP-1 cells (Tripp, R. A. et al. *Nature Immunology* (2001) 2:732-738). In this assay, recombinant RSV G[161-197] induced chemotaxis at levels equivalent to the entire RSV G ectodomain, an activity blocked by pre-incubation with 3D3 or 2D10 at a level comparable to that provided by anti-CX3CR1 polyclonal serum. Table 2 provides the results of this analysis, showing the inhibition of the biological activity by high affinity mAbs binding to the G CCD peptides.

TABLE 2

Chemotaxis Assay Results

| Negative Control (serum free media) | Positive Control (+10% FBS) | RSV G [ecto] | RSV G [161-197] | RSV G [161-197] + 3D3 | RSV G [161-197] + 2D10 | RSV G [161-197] + anti-CX3CR1 |
|---|---|---|---|---|---|---|
| 1.0 | 5.2 | 3.9 | 4.2 | 1.5 | 1.0 | 1.1 |

In more detail, the assay was performed using a transwell insert plate with an 8 µm pore size. Approximately 2 million log-phase THP-1 cells (a human leukemia monocytic cell line) washed twice and suspended in serum-free RPMI 1640 media were added to the upper chamber of the insert plate. Negative control was serum-free media alone to which serum-free media containing 25 nM mAb was added to the lower chamber. As a positive control, media containing 10% FBS was added to the lower chamber. RSV G[ecto] or RSV G[161-1979 samples were added to the lower chamber at a final concentration of 5 nM in serum-free media. For samples with RSV G[161-197] and mAbs, RSV G[161-197] was pre-incubated with 5-fold excess mAb (on a molar basis) for 20 min at room temperature, and then added to serum-free media in the lower chamber, for a final concentration of 5 nM RSV G[161-197] and 25 nM mAb. For samples with anti-CX3CR1 antibody, 2 µL 1 mg/mL anti-CX3CR1 rabbit polyclonal antibody (ThermoFisher Scientific Cat #PA5-19910) was incubated with THP-1 cells for 30 minutes in the upper chamber before being placed into the well. The assembled plates were incubated in a CO2 incubator at 37° C. for 5 h. Cells migrated to the lower chamber were counted, and the chemotactic indices were determined by comparing the fold-increase in cell migration toward the chemoattractant to cell migration toward serum-free media alone. Experiments were performed in at least four biological replicates.

The invention claimed is:

1. An immunogen providing an extended protective lifetime against respiratory syncytial virus (RSV) comprising a complex formed by an RSV G protein or peptidomimetic, wherein said RSV G protein includes a central conserved domain (CCD) with a monoclonal antibody or antigen-binding fragment thereof that blocks interaction of the recombinant RSV G protein with host receptor CX3CR1.

2. The immunogen of claim 1, wherein the CCD comprises residues 131-230 or 167-176 of said RSV G protein.

3. The immunogen of claim 1, wherein the monoclonal antibody or fragment has an affinity associated with a Kd of less than about 1 nM.

4. The immunogen of claim 1, wherein the monoclonal antibody comprises:
   SEQ ID NO: 2 and SEQ ID NO: 16; or
   SEQ ID NO: 4 and SEQ ID NO: 18; or
   SEQ ID NO: 6 and SEQ ID NO: 20; or
   SEQ ID NO: 8 and SEQ ID NO: 22.

5. A vaccine comprising the immunogen of claim 1.

6. A vaccine comprising the immunogen of claim 2.

7. A vaccine comprising the immunogen of claim 3.

8. A vaccine comprising the immunogen of claim 4.

9. The vaccine of claim 1, for use in a method of prophylaxis of respiratory syncytial virus (RSV) infection.

10. The vaccine of claim 1, wherein said mAb is directed to the RSV G protein, which mAb includes an Fc modified to provide an extended effective lifetime in a subject.

11. The vaccine of claim 10, wherein the Fc portion binds to FcRn or mucin.

12. The vaccine of claim 10, wherein the Fc portion comprises a YTE mutation.

13. An immunogen against respiratory syncytial virus (RSV) comprising a complex formed by an RSV G protein or peptidomimetic, wherein said RSV G protein includes a central conserved domain (CCD), wherein the CCD comprises residues selected from the group consisting of residues 131-230 and residues 167-176 of said RSV G protein with a monoclonal antibody or antigen-binding fragment thereof that blocks interaction of the recombinant RSV G protein with host receptor CX3CR1, wherein the monoclonal antibody or fragment has an affinity with a Kd of less than about 1 nM, and wherein said immunogen is for inhalation.

14. The immunogen of claim 13, wherein the monoclonal antibody comprises:
SEQ ID NO: 2 and SEQ ID NO: 16; or
SEQ ID NO: 4 and SEQ ID NO: 18; or
SEQ ID NO: 6 and SEQ ID NO: 20; or
SEQ ID NO: 8 and SEQ ID NO: 22.

15. The immunogen of claim 13, wherein said mAb is directed to the RSV G protein, which mAb includes an Fc modified to provide an extended effective lifetime in a subject.

16. The immunogen of claim 15, wherein the Fc portion binds to FcRn or mucin.

17. The immunogen of claim 15, wherein the Fc portion comprises a YTE mutation.

* * * * *